United States Patent
Lilga et al.

(10) Patent No.: US 9,517,984 B2
(45) Date of Patent: Dec. 13, 2016

(54) CONVERSION OF 2,3-BUTANEDIOL TO 2-BUTANOL, OLEFINS AND FUELS

(71) Applicant: Battelle Memorial Institute, Richland, WA (US)

(72) Inventors: Michael A. Lilga, Richland, WA (US); Guo-Shuh Lee, Richland, WA (US); Suh-Jane Lee, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 130 days.

(21) Appl. No.: 14/678,729

(22) Filed: Apr. 3, 2015

(65) Prior Publication Data

US 2015/0284307 A1 Oct. 8, 2015

Related U.S. Application Data

(60) Provisional application No. 61/975,568, filed on Apr. 4, 2014.

(51) Int. Cl.
| | | |
|---|---|---|
| *C07C 29/60* | (2006.01) | |
| *C07C 29/145* | (2006.01) | |
| *C10L 1/04* | (2006.01) | |
| *C07C 45/29* | (2006.01) | |
| *C10G 45/00* | (2006.01) | |
| *C10G 3/00* | (2006.01) | |
| *C07C 45/52* | (2006.01) | |
| *C07C 29/17* | (2006.01) | |

(52) U.S. Cl.
CPC ............. *C07C 29/145* (2013.01); *C07C 29/60* (2013.01); *C07C 45/29* (2013.01); *C07C 45/52* (2013.01); *C10G 3/44* (2013.01); *C10G 45/00* (2013.01); *C10L 1/04* (2013.01); *C07C 29/172* (2013.01); *C10G 2400/30* (2013.01); *Y02P 30/20* (2015.11)

(58) Field of Classification Search
CPC ............................... C07C 29/60; C07C 29/172
USPC ....................................................... 568/903
See application file for complete search history.

(56) References Cited

U.S. PATENT DOCUMENTS 7,754,928 B2  7/2010  Manzer

OTHER PUBLICATIONS

Emerson et al., "Kinetics of Dehydration of Aqueous 2,3-Butanediol to Methyl Ethyl Ketone," *Ind. Eng. Chem. Prod. Res. Dev.*, vol. 21, No. 3, pp. 473-477, 1982.
Hoang et al., "Conversion of Glycerol to Alkyl-aromatics over Zeolites," *Energy & Fuels*, 3b2, ver. 9, pp. A-F, May 2010.
Kannan et al., "Dehydration of *meso-* & *dl*-Hydrobenzoins & 2,3-Butanediols over Alumina," *Indian J. Chem.*, vol. 7, No. 11, pp. 1164-1166, Nov. 1969.
Lee et al., "The Conversion of 2,3-Butanediol to Methyl Ethyl Ketone over Zeolites," Avelino Corma and Sagrario Mendioroz (eds.), Proceedings of the 12$^{th}$ International Congress of Catalysis, Granada, Spain, Jul. 9-14, 2000, *Studies in Surface Science and Catalysis*, vol. 130, pp. 2603-2608, 2000.
Lundeen et al., "Selective Catalytic Dehydration of 2-Alcohols; a New Synthesis of 1-Olefins," *J. Am. Chem. Soc.*, vol. 85, pp. 2180-2181, Jul. 1963.
Lundeen et al., "Selective Catalytic Dehydration. Thoria-Catalyzed Dehydration of Alcohols," *J. Org.. Chem.*, vol. 32, No. 11, pp. 3386-3389, Nov. 1967.

*Primary Examiner* — Elvis O Price
(74) *Attorney, Agent, or Firm* — Klarquist Sparkman, LLP

(57) ABSTRACT

Embodiments of an integrated method for step-wise conversion of 2,3-butanediol to 2-butanol, and optionally to hydrocarbons, are disclosed. The method includes providing an acidic catalyst, exposing a composition comprising aqueous 2,3-butanediol to the acidic catalyst to produce an intermediate composition comprising methyl ethyl ketone, providing a hydrogenation catalyst that is spatially separated from the acidic catalyst, and subsequently exposing the intermediate composition to the hydrogenation catalyst to produce a composition comprising 2-butanol. The method may further include subsequently exposing the composition comprising 2-butanol to a deoxygenation catalyst, and deoxygenating the 2-butanol to form hydrocarbons. In some embodiments, the hydrocarbons comprise olefins, such as butenes, and the method may further include subsequently exposing the hydrocarbons to a hydrogenation catalyst to form saturated hydrocarbons.

20 Claims, 12 Drawing Sheets

CONVERSION OF 2,3-BUTANEDIOL TO 2-BUTANOL, OLEFINS AND FUELS

CROSS REFERENCE TO RELATED APPLICATION

This application claims the benefit of the earlier filing date of U.S. Provisional Application No. 61/975,568, filed Apr. 4, 2014, which is incorporated by reference in its entirety herein.

ACKNOWLEDGMENT OF GOVERNMENT SUPPORT

This invention was made with government support under DE-AC05-76RL01830 awarded by the United States Department of Energy. The government has certain rights in the invention.

FIELD

This disclosure concerns embodiments of a method for converting 2,3-butanediol to 2-butanol, olefins, and/or hydrocarbon fuels.

BACKGROUND

There are several different direct and indirect pathways to fuels from 2,3-butanediol (BDO) (FIG. 1). Direct conversion of BDO to fuels via known methods is not feasible because catalysts are quickly fouled (e.g., by coking) and lose activity. Direct conversion of BDO to fuels over zeolite catalysts, for example, produces aromatic hydrocarbons, but the catalyst lifetimes are too short to be industrially practical. A need exists for an integrated, step-wise method capable of converting BDO with high yield and selectivity to 2-butanol, olefins, and hydrocarbon fuels.

SUMMARY

Embodiments of a method for converting 2,3-butanediol to 2-butanol, olefins (e.g., butenes), and/or hydrocarbon fuels are disclosed. A composition comprising aqueous 2,3-butanediol is exposed to an acidic catalyst to produce an intermediate composition comprising methyl ethyl ketone. In some embodiments, the composition comprises 50-95 wt % 2,3-butanediol. The acidic catalyst may be a solid acid catalyst, for example, an amorphous or crystalline silicoaluminate, such as H-ZSM-5 zeolite, alumina, various other acidic metal oxides, such as niobic acid, or a combination thereof. The composition may be exposed to the acidic catalyst at a temperature within a range of 150° C. to 500° C. and/or at a pressure within a range of 10 psig to 1200 psig. In some embodiments, the acidic catalyst converts 2,3-butanediol to methyl ethyl ketone or a combination of methyl ethyl ketone and isobutyraldehyde with a selectivity of at least 30%. The catalyst may remain capable of dehydrating at least 80% of the 2,3-butanediol in a composition comprising 90% 2,3-butanediol for at least 50 hours.

The intermediate composition subsequently is exposed to a hydrogenation catalyst to produce a composition comprising 2-butanol. In some embodiments, the hydrogenation catalyst comprises Ru/C, Raney nickel, Re/Ni/C, Pt/C, or a combination thereof. The intermediate composition may be exposed to the hydrogenation catalyst at a temperature within a range of 60° C. to 300° C. and/or at a pressure within a range of 10 psig to 1200 psig.

In some embodiments, the composition comprising 2-butanol is deoxygenated by exposure to a deoxygenation catalyst to produce hydrocarbons. The deoxygenation catalyst may be a solid acid catalyst, such as a crystalline silicoaluminate, such as H-ZSM-5 zeolite, an amorphous silicoaluminate, such as DAVICAT®SIAL 3111 silica-alumina (13% $Al_2O_3$; W.R. Grace & Co.), various other acidic metal oxides, such as niobic acid, or a combination thereof. Deoxygenation may produce saturated or unsaturated hydrocarbons, including aromatic hydrocarbons, unbranched hydrocarbons, branched hydrocarbons, or any combination thereof. Deoxygenation may be performed at a temperature from 200° C. to 500° C. In one embodiment, the temperature is within a range of 200° C. to 275° C., and the hydrocarbons comprise unbranched C4-C12 olefins, branched C4-C12 olefins, or a combination thereof. In another embodiment, the temperature is within a range of 350° C. to 500° C., and the hydrocarbons comprise at least 40% aromatic hydrocarbons. In yet another embodiment, the temperature is between 275° C. and 350° C., and the hydrocarbons comprise a mixture of aromatics, unbranched olefins, and branched olefins.

In some embodiments, the hydrocarbons include olefins, and the olefins are further converted to saturated hydrocarbons by exposure to a subsequent hydrogenation catalyst. The subsequent hydrogenation catalyst may comprise Ru/C, Raney nickel, Re/Ni/C, Pt/C, or a combination thereof. Hydrogenation may be performed at a temperature within a range of 100° C. to 300° C.

In one embodiment, the catalysts are disposed individually in columns arranged in series. In another embodiment, the catalysts are spatially disposed sequentially within a single column.

The foregoing and other objects, features, and advantages of the invention will become more apparent from the following detailed description, which proceeds with reference to the accompanying figures.

DETAILED DESCRIPTION

Figure 1:
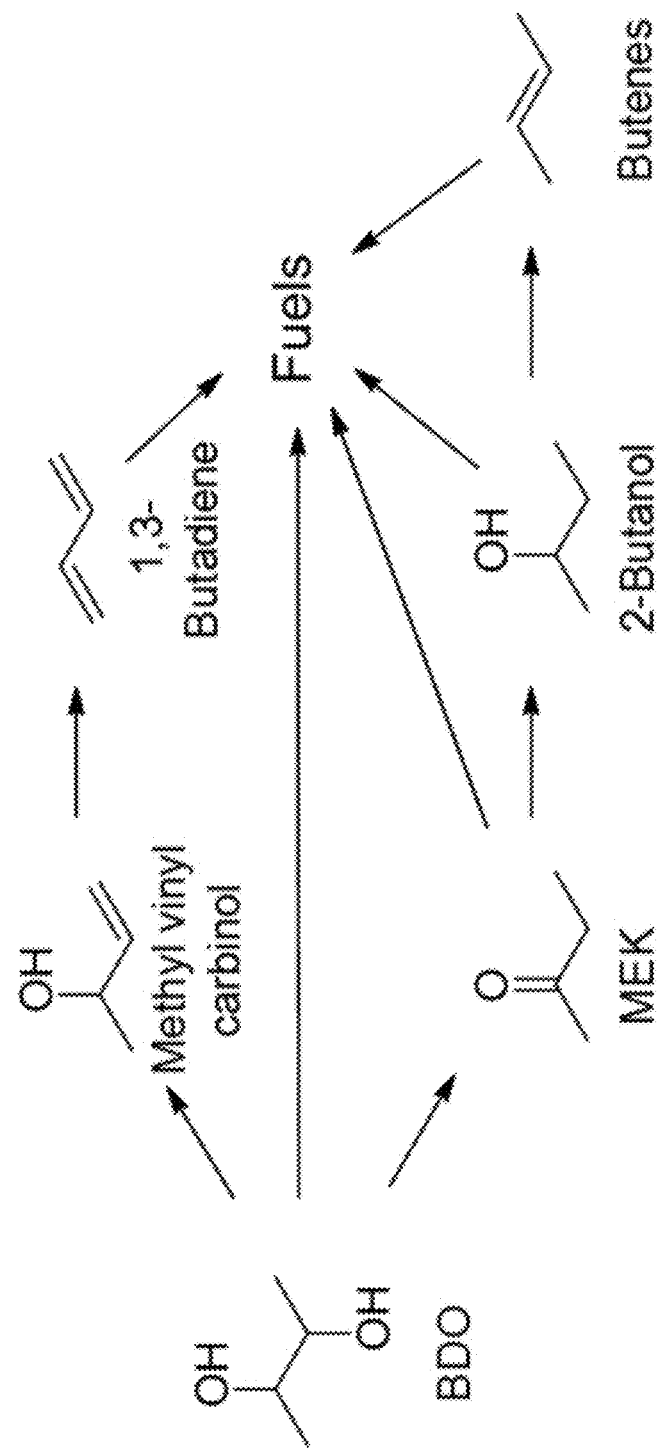
FIG. 1 shows direct and indirect pathways to fuels from 2,3-butanediol (BDO).

Disclosed herein are embodiments of catalysts and methods for converting BDO to 2-butanol, olefins, and hydrocarbon fuels (FIG. 1). In particular, embodiments of an integrated method for step-wise conversion of BDO to 2-butanol and/or hydrocarbons are disclosed. The hydrocarbons may include saturated and unsaturated hydrocarbons, such as olefins (including butenes) and aromatic compounds. 2-Butanol and/or olefins subsequently can be converted to aromatic hydrocarbons, paraffinic and/or isoparaffinic hydrocarbons, or a mixture thereof, depending on processing temperatures.

I. Definitions and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of reactants, parameters such as temperatures, pressures, percentages, and so forth, as used in the specification or claims are to be understood as being modified by the term "about." Unless otherwise indicated, all percentages are percent by weight. Unless otherwise indicated, non-numerical properties, such as amorphous, as used in the specification or claims are to be understood as being modified by the term "substantially," meaning to a great extent or degree. Accordingly, unless otherwise indicated, implicitly or explicitly, the numerical parameters and/or non-numerical properties set forth are approximations that may depend on the desired properties sought, limits of detection under standard test conditions/methods, limitations of the processing method, and/or the nature of the parameter or property. When directly and explicitly distinguishing embodiments from discussed prior art, the embodiment numbers are not approximates unless the word "about" is recited.

Amorphous: Non-crystalline, having no or substantially no molecular lattice structure. Amorphous solids lack a definite crystalline structure and a well-defined melting point.

Aromatic or aryl compound: An unsaturated cyclic hydrocarbon having alternate single and double bonds. Benzene, a 6-carbon ring containing three double bonds and three single bonds, is a typical aromatic compound.

BDO: 2,3-butanediol

Calcine: As used herein, the term "calcine" means to heat a solid to a temperature below its melting point remove crystalline waters of hydration and and/or to oxidize some metals.

Catalyst: A substance that increases the rate of a chemical reaction without itself being consumed or undergoing a chemical change. A catalyst also may enable a reaction to proceed under different conditions (e.g., at a lower temperature) than otherwise possible.

Hydrocarbon: A compound consisting of hydrogen and carbon. Hydrocarbons include saturated hydrocarbons (e.g., alkanes (paraffins), cycloalkanes) and unsaturated hydrocarbons (e.g., alkenes (olefins), and/or aromatic compounds). The hydrocarbons may be branched or unbranched.

IBA: Isobutyraldehyde

Isoparaffin: A branched-chain saturated hydrocarbon.

MEK: methyl ethyl ketone

Olefin: An unsaturated aliphatic hydrocarbon having one or more double bonds. Olefins with one double bond are alkenes; olefins with two double bonds are alkadienes or diolefins. Olefins may be branched or linear.

Paraffin: A saturated hydrocarbon. As used herein, the term "paraffin" refers to unbranched alkanes.

Raney nickel: A solid, fine-powder catalyst comprising a nickel-aluminum alloy, e.g., an alloy comprising ≥89% Ni and 6-9% Al. Raney nickel (W.R. Grace and Company. Columbia, Md.) is also known as a "sponge-metal catalyst" because the individual particles include irregular pores of varying sizes. Raney nickel has an average Ni surface area of 100 m²/g.

SCCM: standard cubic centimeters per minute

Selectivity: As used herein, selectivity refers to the ability of a catalyst to direct a reaction to preferentially form a particular product. For example, suppose a catalyst can dehydrate compound A to form compound B, compound C, or a mixture of compounds B and C. If the catalyst has a compound B selectivity of 90%, compound A will be dehydrated to form 90% compound B and 10% compound C. Selectivity may be determined by analysis of the products formed by the reaction. In certain examples herein, selectivity was determined by gas chromatography/mass spectrometry of reaction products.

Silicoaluminate: A mineral comprising aluminum, silicon, and oxygen, plus countercations; aluminosilicate is a synonym.

Solid acid catalyst: A solid catalyst including Brønsted acid (proton donor) and/or Lewis acid (electron-pair acceptor) sites, e.g., catalysts including protons or acidic groups, such as sulfonic acid groups. Some zeolites, for example, are solid acid catalysts as described below.

WHSV: Weight hourly space velocity. WHSV is defined as the weight of feed flowing per weight of catalyst per hour.

Zeolite: The term "zeolite" refers to any one of a group of microporous aluminosilicates. Some zeolites include cations (e.g., $H^+$, group IA cations or IIA cations) in the pores. Zeolites are often referred to as molecular sieves since they can be used to selectively sort molecules by size based on size exclusion from the pores. Zeolites may be characterized by pore size and/or by the Si/Al ratio. H-ZSM-5 is an acidic zeolite having medium-size pores with channels defined by 10-membered rings of alternating silicon (or aluminum) and oxygen atoms. H-ZSM-5 has a high $Si^{4+}/Al^{3+}$ ratio (e.g., 20-30) with a proton for each $Al^{3+}$ cation to keep the material charge neutral.

II. Dehydration of BDO to MEK

MEK can be produced by dehydration of BDO with acidic catalysts. BDO may be obtained from any source. For example, BDO may be obtained as a byproduct of CO fermentation, a byproduct of anaerobic microbial saccharide (e.g., glucose, lactose, galactose) fermentation, or by any other process. All isomers of BDO may be used, i.e., d-, l-, and meso isomers.

BDO is exposed to the catalyst by bringing BDO, in liquid or gas phase, in contact with the catalyst for an effective period of time at an effective temperature and/or pressure for dehydration to occur as discussed below. BDO may be exposed to the catalyst by any suitable means, including combining BDO and the catalyst in a closed vessel, or flowing BDO across and/or through a catalyst bed disposed in a column.

The reaction mechanism involves an acid-catalyzed pinacol rearrangement in which initial dehydration is followed by a hydride shift. A side reaction is the shift of a methyl group instead of hydride to form isobutyraldehyde (IBA). The extent to which this side reaction occurs depends on temperature and the steric environment in the intermediate carbocation.

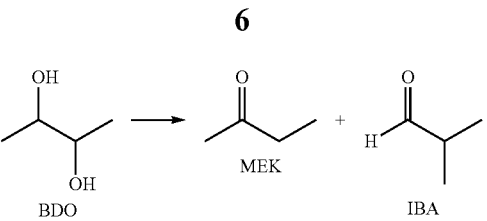

MEK yields exceeding 90 mol % have been obtained in homogeneous aqueous solutions containing approximately 50 g/L BDO and 0.48-1.9 M $H_2SO_4$ at 148-180° C. (Emerson, Ind. Eng. Chem. Prod. Res. Dev. 21, 473-477, 1982).

The pinacol rearrangement can also occur with solid acid catalysts, such as solid Brønsted and/or Lewis acid catalysts. Suitable solid acid catalysts include, but are not limited to, acidic zeolites (e.g., H-ZSM-5), montmorillonite, aluminas, silicas, sulfated zirconia, heteropolyacids, metal oxides, metal salts such as metal sulfides, metal sulfates, metal sulfonates, metal nitrates, metal phosphates, metal phosphonates, metal molybdates, metal tungstates, and certain cation exchange resins (e.g., cation exchange resins that are stable at temperatures up to 100-170° C., such as styrene-divinylbenzene copolymer-based cation exchange resins). In some embodiments, an acidic zeolite or alumina-based catalyst is used. The zeolite may have a Si/Al ratio of 20-1200, e.g., H-ZSM-5 (23), H-ZSM-5 (30). In some embodiments, Si/Al ratios at the lower end of the range with increased acidity may dehydrate a greater percentage of BDO to form MEK and/or IBA.

Catalyst effectiveness is dependent, at least in part, on temperature and/or pressure. In some embodiments, acidic zeolite and/or alumina catalysts effectively dehydrate BDO at a temperature ≥150° C., such as ≥240° C., ≥260° C. or ≥280° C. In certain embodiments, the temperature is within a range of 150° C. to 500° C., such as from 240° C. to 300° C. or from 260° C. to 300° C. It was noted that, at temperatures from 240-300° C., the d/l isomers of BDO converted more readily than the meso isomer.

In some embodiments, BDO dehydration is performed under a hydrogen atmosphere at increased pressure, such as a pressure within a range of 10 psig to 1200 psig. In a continuous flow reactor wherein the catalyst was disposed in a column, a pressure of 200 psig was used.

Although the desired reaction is dehydration, the inventors unexpectedly discovered that addition of at least some water to BDO increases MEK selectivity compared to anhydrous BDO, which favors condensation reactions and/or initial conversion to aromatic compounds. This result was also unexpected because aluminum-containing acidic catalysts (e.g., zeolites) may be dealuminated when water is present, thereby deactivating the catalyst. Dealumination, however, can be minimized by controlling the amount of water in the BDO composition. Thus, in some embodiments, an aqueous BDO composition including 50-95% BDO, such as 70-90% BDO, is used. When the feed is an aqueous composition comprising 50-95% BDO, an alumina or acidic zeolite catalyst may convert BDO to MEK and IBA with a selectivity of at least 30%, at least 50%, at least 60%, at least 70%, or at least 80%.

In some embodiments, an H-ZSM-5 catalyst retains activity when exposed to a feed comprising 90% BDO and 10% water for at least 50 hours, at least 75 hours, or at least 100 hours. In one example, a H-ZSM-5 (23) catalyst remained capable of dehydrating aqueous 90% BDO for more than 120 hours at 300° C. Conversion of both d/l and meso isomers was complete, with greater than 60% selectivity to MEK and IBA.

In some embodiments, the acidic catalyst is disposed within a column, the catalyst in the column is heated to a temperature ≥200° C., and an aqueous BDO composition is flowed through the column at a weight hourly space velocity (WHSV) ranging from 0.1 to 10 h$^{-1}$. In certain examples, the WHSV ranges from 2 to 4 h$^{-1}$.

III. Reduction of MEK to 2-Butanol

MEK is converted to 2-butanol under mild reduction conditions. If IBA is present, it may be reduced to isobutanol. Hydrogenation catalysts include, but are not limited to, catalysts comprising Co, Cr, Cu, Ir, Ni, Os, Pd, Pt, Re, Rh, Ru, and combinations thereof. Effective catalysts include Ru/C, Raney nickel, Re/Ni/C, Pt/C, Pd/C, and combinations thereof. In some embodiments, the catalyst is 5% Ru/C, Raney nickel, 2.5% Re/2.5% Ni/C, 5% Pt/C, or 1.5% Pd/C.

MEK is exposed to the catalyst by bringing MEK, in liquid or gas phase, in contact with the catalyst for an effective period of time at an effective temperature and/or pressure for hydrogenation to occur as discussed below. MEK may be exposed to the catalyst by any suitable means, including combining MEK and the catalyst in a closed vessel, or flowing MEK across and/or through a catalyst bed disposed in a column.

The MEK feed is combined with hydrogen. Reduction can be performed at temperatures within a range of 60° C. to 300° C., such as from 80° C. to 280° C., 100° C. to 220° C., 150° C. to 200° C., or from 120° C. to 160° C. In some embodiments, the pressure is at least 50 psig, such as at least 100 psig, at least 200 psig, or at least 300 psig, such as within a range of 10 psig to 1200 psig. Increasing pressure and/or lowering temperature may raise the percent yield of 2-butanol by increasing the solubility of hydrogen in the MEK feed.

In some embodiments, at least 60%, at least 70%, at least 80%, or at least 90% of the MEK is reduced, and the product comprises at least 40%, at least 60%, at least 80%, or even at least 90% 2-butanol. Side products may include, for example, residual MEK, IBA, and/or isobutanol. In certain examples, at least 70%, such as 70-99.5% or 90-99.5%, of the MEK is reduced, and the product comprises at least 70%, such as 70-98% or 90-98%, 2-butanol.

In some embodiments, the hydrogenation catalyst is disposed within a column, the catalyst is heated to a temperature within a range of 60° C. to 300° C., and a composition comprising MEK is flowed through the column at a weight hourly space velocity (WHSV) ranging from 0.1 to 10 h$^{-1}$. In certain examples, the WHSV ranges from 1.5 to 9 h$^{-1}$, or from 1.5 to 3.5 h$^{-1}$.

IV. Integrated, Step-Wise Conversion of BDO to 2-Butanol

An integrated, step-wise conversion of BDO to 2-butanol comprises converting an aqueous BDO feed by an acidic catalyst to an intermediate composition comprising MEK, and subsequently reducing MEK to 2-butanol with a hydrogenation catalyst. The acidic catalyst and the hydrogenation catalyst are spatially separated such that the feed is exposed sequentially to the acidic catalyst and then to the hydrogenation catalyst. Spatial separation facilitates step-wise conversion and enhances the 2-butanol yield. If the aqueous BDO composition is exposed simultaneously to the acidic catalyst and the hydrogenation catalyst, undesirable side reactions can occur. For example, when the catalysts are mixed or a bifunctional catalyst (e.g., Pt/H-ZSM-5) is utilized, 2-butanol may be further dehydrated to butenes by the acidic catalyst, which in turn may be reduced to butanes by the hydrogenation catalyst.

In some embodiments, a composition comprising aqueous 2,3-butanediol is exposed to an acidic catalyst to form an intermediate composition, which is rich in MEK. The aqueous BDO feed may comprise 50-95% BDO. The intermediate composition subsequently is exposed to a hydrogenation catalyst to produce a composition comprising at least 40% 2-butanol, such as at least 50% 2-butanol. In certain examples, the composition may further include 5-15% isobutanol.

The acidic catalyst may be a solid acid catalyst. In some examples, the acidic catalyst is a crystalline silicoaluminate, such as an H-ZSM-5 zeolite (e.g., H-ZSM-5 (23) or H-ZSM-5 (30)), an amorphous silicoaluminate, such as DAVICAT®SIAL 3111 silica-alumina (13% Al$_2$O$_3$; W.R. Grace & Co.), alumina, various acidic metal oxides, such as niobic acid (i.e., hydrated niobium pentoxide; Nb$_2$O$_5$.nH$_2$O), or a combination thereof. In some embodiments, the BDO composition is exposed to the acidic catalyst at a temperature within a range of 150° C. to 500° C., such as from 200° C. to 350° C., or from 240° C. to 300° C. The pressure may range from 10 psig to 1200 psig, such as from 20-1000 psig, 50-500 psig, 100-300 psig, or 150-250 psig.

In some embodiments, the hydrogenation catalyst comprises Ru/C, Raney nickel, Re/Ni/C, Pt/C, or a combination thereof. In certain examples, the hydrogenation catalyst is 5% Ru/C, Raney nickel, 2.5% Re/2.5% Ni/C, or 5% Pt/C. The intermediate composition may be exposed to the hydrogenation catalyst at a temperature within a range of 60° C. to 300° C., such as from 100° C. to 220° C., or from 120° C. to 160° C.

Step-wise conversion of BDO to 2-butanol may be a continuous or substantially continuous process in which a BDO feed composition flows across or through an acidic catalyst bed to form an intermediate composition, and then the intermediate composition subsequently flows across or through a hydrogenation catalyst bed. In some embodiments, a first column containing a packed acidic catalyst bed is prepared, and a second column containing a packed hydrogenation catalyst bed is prepared. Each of the first column and the second column comprises an inlet and an outlet. The first column outlet is fluidly connected to the second column inlet. An aqueous BDO composition is flowed through the first column to form an intermediate composition. The intermediate composition exits through the first column outlet, then flows through the second column inlet into the second column. A product comprising 2-butanol exits through the second column outlet. In some embodiments, the catalyst bed in the first column is heated to a temperature within a range of 150° C. to 500° C. and the catalyst bed in the second column is heated to a temperature within a range of 60° C. to 300° C. Each column independently may be operated at a pressure within a range of 10 psig to 1200 psig.

In some embodiments, the BDO composition is introduced into the first column at ambient temperature. In other embodiments, the BDO composition is preheated before flowing into the first column. For example, the BDO composition may be heated to a temperature within a range of 150° C. to 250° C.

A person of ordinary skill in the art will appreciate that BDO composition and intermediate composition flow rates through the first and second columns are affected by a number of variables including, but not limited to, catalyst composition, column dimensions, temperature, pressure, feed concentration, and combinations thereof. In some embodiments, the WHSV ranges from 0.1 to 10, such as from 1 to 8 h$^{-1}$ or from 3 to 5 h$^{-1}$. In one example, the WHSV was 4 h$^{-1}$.

Hydrogen is flowed concurrently through at least the second column. In certain embodiments, hydrogen is flowed concurrently through the first and second columns. The hydrogen flow rate is affected by a number of variables including, but not limited to catalyst composition, column dimensions, temperature, pressure, BDO feed concentration, and combinations thereof. Suitable hydrogen flow rates range from 20 sccm to 1,000 sccm, such as from 200 sccm to 600 sccm, or from 300 sccm to 500 sccm. The hydrogen flow rate, BDO composition flow rate, and/or intermediate composition flow rate may be selected to achieve a desired contact time in each of the columns.

In some embodiments, the second column (or both the first and second columns) is purged with hydrogen before the BDO composition is introduced into the first column. The column(s) may be heated during the hydrogen purge to regenerate the catalyst(s), e.g., by removing adsorbed water and/or by-products adsorbed during prior use. In some embodiments, the second column is heated and purged with hydrogen for at least 1 hour prior to use.

A chilled receiver vessel may be fluidly connected to the second column outlet so that product exiting the second column is chilled and condensed to a liquid. Alternatively, products may be collected by adsorption onto a suitable adsorbent (e.g., a Carbopack™ (graphitized carbon) bed) at a reduced temperature (e.g., less than 50° C.), and subsequently desorbed by heating the adsorbent.

In one embodiment, an acidic catalyst and a hydrogenation catalyst are disposed in a single column with the hydrogenation catalyst positioned in the column distal to the acidic catalyst. The acidic and hydrogenation catalysts may be selected so that one temperature range is suitable for both catalysts. Alternatively, the column may be designed such that independent temperature control of a proximal portion and a distal portion of the column is achievable. The column may be heated and purged with hydrogen for at least an hour prior to use. An aqueous BDO composition and hydrogen gas are flowed concurrently into the column. The BDO feed composition is exposed first to the acidic catalyst and then to the hydrogenation catalyst, and is converted step-wise to 2-butanol. The product comprises an organic phase and an aqueous phase, with 2-butanol in both phases.

In some embodiments, integrated step-wise conversion of BDO to 2-butanol results in at least 90% conversion of BDO to an intermediate product comprising at least 40% MEK, such as 40-90% MEK and 5-10% IBA. In the second step, 75-100% of the MEK and IBA are reduced to 2-butanol and isobutanol, respectively. Thus, the overall process may produce 2-butanol with an overall percent yield of at least 30%, such as an overall percent yield of 30-90%.

V. Conversion of 2-Butanol to Olefins, Aromatics, and/or Fuels

2-Butanol is deoxygenated to form olefins, including butenes, and aromatics. In one embodiment, a composition comprising 2-butanol, which is obtained from the sequential dehydration and hydrogenation of an aqueous BDO feed composition is used without further purification. In another embodiment, a composition obtained from the sequential dehydration and hydrogenation of an aqueous BDO feed composition is fractionated, and a fraction enriched in 2-butanol subsequently is deoxygenated to form olefins and aromatics. In another embodiment, the olefins and aromatics are hydrogenated to form hydrocarbon fuels.

In some embodiments, deoxygenation is performed with an acidic catalyst. Suitable catalysts include, but are not limited to, acidic zeolites (e.g., with a Si/Al ratio of 20-30), alumina, niobic acid, and amorphous silicoaluminates. In one example, the catalyst was H-ZSM-5 (30) with an alumina binder.

2-Butanol is exposed to the catalyst by bringing 2-butanol, in liquid or gas phase, in contact with the catalyst for an effective period of time at an effective temperature and/or pressure for deoxygenation to occur as discussed below. 2-Butanol may be exposed to the catalyst by any suitable means, including combining 2-butanol and the catalyst in a closed vessel, or flowing 2-butanol across and/or through a catalyst bed disposed in a column.

Deoxygenation may be performed at a temperature of at least 200° C., or at least 250° C., such as within a range of 200° C. to 500° C. It was discovered that the product composition is dependent on temperature. Higher temperatures favor formation of aromatic compounds, whereas lower temperatures favor normal and branched C4-C12 olefins. Thus, in one embodiment as illustrated for HZSM-5, deoxygenation is performed at a temperature of at least 350° C. to produce a composition having an organic phase comprising aromatic compounds. In another embodiment, deoxygenation is performed at a temperature less than 275° C. to form a composition having an organic phase comprising unbranched and branched olefins. In one example, deoxygenation at 250° C. gave a hydrocarbon product consisting essentially of normal and branched C4-C12 olefins. The olefins can be subsequently hydrotreated to provide a mixture of paraffins and isoparaffins as a blend stock for jet fuel. In yet another embodiment, deoxygenation is performed at a temperature from 275° C. to 350° C. to produce a composition having an organic phase comprising a mixture of aromatic compounds and olefins. This mixture can be subsequently hydrotreated and optionally fractionated to provide, depending on conditions, a mixture of aromatics, cyclic and normal paraffins and isoparaffins as a fuel blend stock.

In some embodiments, 2-butanol is converted to hydrocarbons in a continuous or substantially continuous process in which a 2-butanol feed composition flows across or through an acidic catalyst bed to form hydrocarbons. A packed acidic catalyst bed is disposed in a column, and the catalyst bed is heated to a temperature within a range of 200° C. to 500° C., wherein the selected temperature depends at least in part on the desired end product composition. The 2-butanol feed composition is flowed through the heated column, e.g., at a pressure within a range of 10-1200 psig. The catalyst may remain capable of deoxygenating 2-butanol for at least 50 hours, at least 75 hours, or at least 100 hours. In one example, an H-ZSM-5 (30) catalyst with an alumina binder remained capable of deoxygenating 2-butanol at 400° C. for more than 103 hours with no apparent deactivation.

A person of ordinary skill in the art will appreciate that the flow rate through the column is affected by a number of variables including, but not limited to, catalyst composition, column dimensions, temperature, pressure, feed concentration, and combinations thereof. In some embodiments, the WHSV ranges from 0.1 to 10 h$^{-1}$. In one example, the WHSV was 2.5 h$^{-1}$.

In some embodiments, at least 50%, at least 60%, at least 70%, at least 80%, at least 90%, or at least 95% of 2-butanol is converted to hydrocarbons. In certain examples, substantially all of the 2-butanol is converted to hydrocarbons.

Hydrotreating can be performed by combining the olefins and/or aromatics with hydrogen and exposing them to a hydrogenation catalyst. Suitable catalysts include Ru/C, Raney nickel, Re/Ni/C, Pt/C, or a combination thereof. Hydrogenation is performed at temperatures ranging from 100° C. to 250° C., such as from 150° C. to 250° C. In some embodiments, the pressure is within a range of 100 psig to 1200 psig, such as from 500 psig to 1000 psig. Hydrotreating may be performed at a WHSV from 0.1 to 10 h$^{-1}$, such as from 1 to 5 h$^{-1}$. In one embodiment, the olefins comprise butenes and hydrotreating produces butanes.

In some embodiments, a step-wise conversion of BDO to hydrocarbon fuels is performed. In one embodiment, an aqueous BDO feed flows through a first column containing a packed acidic catalyst bed to form an intermediate composition comprising MEK. The intermediate composition flows from the first column through a second column containing a packed hydrogenation catalyst bed to form a product comprising 2-butanol. The 2-butanol product then flows from the second column through a third column containing a packed acidic catalyst bed to produce a product comprising olefins and aromatics. The olefins and aromatics may subsequently be hydrotreated in a fourth column containing a packed hydrogenation catalyst bed to provide a mixture of paraffins and isoparaffins. Optionally, the olefins and aromatics may be fractionated before hydrotreating so that only fuel-range hydrocarbons are hydrogenated. Each column's internal temperature and pressure are independently selected as previously described.

In another embodiment, a column including three spatially separated catalyst regions is prepared. The first catalyst region comprises an acidic catalyst, the second catalyst region comprises a hydrogenation catalyst, and the third catalyst region comprises an acidic catalyst. The acidic catalysts in the first and third regions may be the same or different. The catalyst regions are positioned such that a feed flowing into the column will be exposed sequentially to the first catalyst, the second catalyst, and finally the third catalyst. The catalysts may be selected so that one temperature range is suitable for all three catalysts and for the desired product composition, e.g., primarily aromatics, olefins, or a combination thereof. Alternatively, the column may be designed such that independent temperature control of the first, second, and third catalyst regions of the column is achievable. An aqueous BDO composition is flowed into the column. Hydrogen gas is concurrently flowed through the column. As the BDO composition flows through the column, it is sequentially dehydrated, hydrogenated, and deoxygenated to form a product comprising olefins and aromatics. Optionally, the column may include a further spatially separated catalyst region, wherein the fourth catalyst region comprises a hydrogenation catalyst. The hydrogenation catalysts in the second and fourth regions may be the same or different. In such embodiments, the BDO composition is sequentially dehydrated, hydrogenated, deoxygenated, and then further hydrogenated to form a product comprising saturated hydrocarbons.

VI. Examples

Materials

Methyl ethyl ketone (99+%) and 2,3-butanediol were obtained from Aldrich Chemical Co. The Aldrich BDO (98%) was a mixture of meso-(~76%) and racemic d/l isomers (~24%). BDO obtained from LanzaTech was a d/l mixture (~95%) and contained very little meso isomer (~3%).

Pyroprobe GC/MS Apparatus and General Procedure

The pyroprobe unit used in this work was a CDS Analytical, Inc. Series 5000 pyroprobe (model 5200). The pyroprobe was equipped with an optionally used downstream heated catalyst bed, and a heated Carbopack adsorbent bed located between the catalyst bed and the gas chromatograph (GC) inlet. The GC used was an Agilent Technologies 7890A GC system, equipped with an Agilent Technologies 5975C inert XL mass spectroscopic (MS) detector with Triple-Axis Detector. The GC column used for product separation was a DB5 column.

The feedstock was 10 wt % BDO (Aldrich) in deionized (DI) water. The catalyst (~2 mg of powder) was loaded into a quartz tube (25 mm long×1.9 mm I.D.; open at both ends), and held in position using a quartz wool plug on both ends of the powder layer. Approximately 1 μL of feed solution was subsequently dispensed onto the back quartz wool plug and then loaded into the pyroprobe wand with the liquid-containing end down, so that upon heating the liquid feed vapors would be carried through the catalyst bed. After the tube was loaded into the pyroprobe wand, the end of the wand was inserted into the pyroprobe unit and sealed. Helium carrier gas flowed through the probe wand and over the quartz wool plugs and catalyst. Upon initiation of the unit, a heating coil encircling the quartz tube, rapidly heated the tube and its contents to ~600° C. and maintained it at that temperature for usually 15 seconds. Carrier gas flows were typically 20 ccm of He through the pyroprobe. Reactant and product vapors were rapidly carried out of the quartz tube and adsorbed onto a Carbopack bed at 40° C., then later desorbed from the adsorbent bed at 300° C. The desorbed products were carried into the GC/MS unit for separation and analysis. Area % reports were generated for % conversion of BDO and product selectivity to 1,3 butadiene, methyl vinyl carbinol, MEK, and isobutyraldehyde (IBA). Aldrich BDO was a mixture of d/l and meso isomers. Early analyses integrated over both isomers (reported as BDO) until method improvements allowed separate quantification.

Continuous Flow Reactor

A small, continuous fixed bed flow reactor was constructed to investigate chemical conversions on a scale larger than the pyroprobe with control of feed rates, temperatures, and pressures. An isocratic HPLC pump was used to introduce liquid feeds, including BDO, MEK, and 2-butanol. The reactor was made of stainless steel tubing with ¼" outer diameter and 8" length. The catalyst bed was positioned approximately in the middle of the tube, held in place by quartz wool plugs and 80-100 mesh Pyrex glass beads, both above and below the catalyst bed. The packed reactor tube was placed approximately in the middle of an electrically heated furnace. The furnace control thermocouple was located on the outside skin of the reactor tube, adjacent to the catalyst bed. A mass flow controller was used to control nitrogen, air, or H$_2$ carrier gases at flow rates up to 1000 sccm. The system also included two chilled receiver vessels for collecting liquid product samples alternately without disturbing the experiment. The reactor pressure was maintained with use of a back pressure regulator. Effluent gas rates were measured with a soap bubble flow meter and stopwatch and gas samples obtained using a gas-tight syringe. Gas samples were analyzed on a Carle Series 400 AGC using the #160-Sp application (refinery gas analysis). Liquid samples were analyzed on an Agilent 6890 GC with an FID detector or on the Agilent GC/MS described above.

Example 1

Direct Conversion of BDO to Fuels

Direct conversion of BDO to hydrocarbons was attempted over H-ZSM-5 catalyst. In a typical run, 1.28 g of H-ZSM-5 (Si/Al=30)/$Al_2O_3$ binder was loaded into a ¼ inch tube reactor. The feed rate was 0.05 mL/min and the reactor was heated to 400° C. Samples were collected over a period of 75 h.

It was found that the product distributions for experiments using either BDO or MEK as pure feeds were nearly identical, suggesting that MEK is the likely intermediate in BDO conversion. The results of both experiments are shown in Table 1. As can be seen in Table 1, the catalyst was only active for about 6 h for the production of hydrocarbons. After that, the catalyst was only active for BDO dehydration to MEK. Without wishing to be bound by a particular theory of operation, it is believed that coke formation changed the selectivity of the catalyst. While it is possible to continuously regenerate the catalyst, for example in a side stream removed from a fluidized bed reactor, this mode of operation is not optimal. This consideration in combination with the observation that this process would form aromatics, rather than the desired isoparaffins, prompted a focus for the remainder of the work on indirect methods via MEK derivatives (such as 2-butanol) or butadiene.

TABLE 1

Comparison of the product distribution using either BDO or MEK as pure feed over H-ZSM-5(30)/$Al_2O_3$ catalyst in a continuous reactor.

| Products | BDO | | | MEK | | |
|---|---|---|---|---|---|---|
| | 3.0 h | 6.0 h | 18 h | 3.5 h | 6.1 h | 16 h |
| % MEK | 0.0 | 24 | 49 | 0.0 | 24 | 57 |
| % Benzene | 5.5 | 0.0 | 0.0 | 6.3 | 1.1 | 0.0 |
| % Toluene | 15 | 5.5 | 0.0 | 30 | 7.4 | 0.9 |
| % Xylene | 24 | 15 | 0.0 | 30 | 15 | 3.0 |
| % Naphthalenes | 14 | 1.9 | 0.0 | 10 | 3.4 | 0.0 |

Example 2

Conversion of BDO to MEK in a Pyroprobe

Catalyst evaluations were performed using three configurations: 1) with catalyst in the heated pyroprobe, (2) with an inert support in the pyroprobe and the active catalyst in a small heated post reactor, and (3) with catalyst in both the pyroprobe and post reactor.

In the first configuration, 2 mg of H-ZSM-5 ($SiO_2$/$Al_2O_3$=30) was loaded in the pyroprobe and 1 µL of 10% BDO in water was injected onto the catalyst. The probe was heated rapidly to either 300 or 500° C. for 15 sec. Helium carrier gas (20 mL/min) was used to sweep the product onto a trap for collection (trap temperature=40° C.). The product was desorbed (340° C. for 2 minutes) and transferred to a GC/MS injector (Agilent 7890A GC, split ratio=100/1, initial temperature=40° C., hold for 5 minutes, final temperature=250° C., hold for 3 minutes, carrier gas=1 mL/min He). The MS detector was an Agilent 5975C.

At 300° C., the reaction achieved 97.3% BDO conversion with 78.6% selectivity to MEK, 10.5% isobutyraldehyde, 1.1% butane, and 3.4% acetic acid. At 500° C., the BDO conversion was close to 100% with 56% MEK and 40% aromatics. No aldol condensation products were observed. The background reaction of BDO over various supports such as SiC, silica, $TiO_2$ and $ZrO_2$ and quartz wool were qualitatively checked in the pyroprobe. For quartz wool, the BDO was 25.8% converted to a mixture of MEK (major product) and IBA. With silica gel as catalyst, 95% BDO conversion with 8% butadiene and 85% of MEK and IBA were observed. Y-zeolite, 10% Ni-ZSM-5, and 10% Fe-ZSM-5 at 500° C. did not form a significant amount of MEK. Na-ZSM-5 (with 20% $ZrO_2$) generated MEK, IBA, and some acetaldehyde.

In the second configuration, 25 mg H-ZSM-5 ($SiO_2$/$Al_2O_3$=30) was loaded into the post reactor and 1 µL of 10% BDO was loaded onto quartz wool in the pyroprobe. The probe was heated to 300° C. under a flow of He (20 mL/min) and the BDO vapor was passed into the post reactor, also at 300° C. The BDO conversion was near 100% with MEK as the major product. Other products detected by GC/MS included hydrocarbons and aromatics. The products in the gas phase included propane, butane, butenes, pentene, 1,2-dimethylpropane, MEK, and IBA In the third configuration, 2 mg of H-ZSM-5 ($SiO_2$/$Al_2O_3$=30) was loaded into the pyroprobe and 25 mg of the same catalyst was loaded in the post reactor. 1 µL of 10% BDO in water was injected onto the catalyst in the pyroprobe. The probe was heated to 500° C. for 15 second and the post reactor was heated to 300° C. In this two stage catalytic reactor, BDO was 100% converted to mostly aromatics with some C3 and C4 hydrocarbon gases also formed.

The mixed oxide $PrCeO_x$ was tested in the pyroprobe with 1 µL of 10% BDO in water as feed. The probe was heated to 400° C. The BDO conversion was about 40% with ethanol, acetaldehyde, acetic acid, acetone, epoxides, and ketals being detected as products. It appears that $PrCeO_x$ functioned primarily as an oxidation catalyst, cleaving the vicinal diol.

A series of runs were performed using a $La_2O_3$/$ZrO_2$/$Al_2O_3$ catalyst since this catalyst can produce both butadiene and MEK. 2 mg of the $La_2O_3$/$ZrO_2$/$Al_2O_3$ catalyst was used in the pyroprobe, 1 µL of 10% BDO in water was used, and the probe temperature was 500° C. A multiple run study was conducted. Results were variable, but good yields of butadiene were observed (Table 2).

TABLE 2

Multiple run study of BDO with $La_2O_3$/$ZrO_2$/$Al_2O_3$ catalyst in pyroprobe.

| Products | Run 1 | Run 2 | Run 3 |
|---|---|---|---|
| % MEK + IBA | 38.5 | 85 | 68 |
| % 1,3-Butadiene | 42.7 | 6 | 14.8 |
| % BDO | 0.63 | 5 | 9 |

Example 3

Conversion of BDO to MEK in a Parr Reactor

Figure 2:
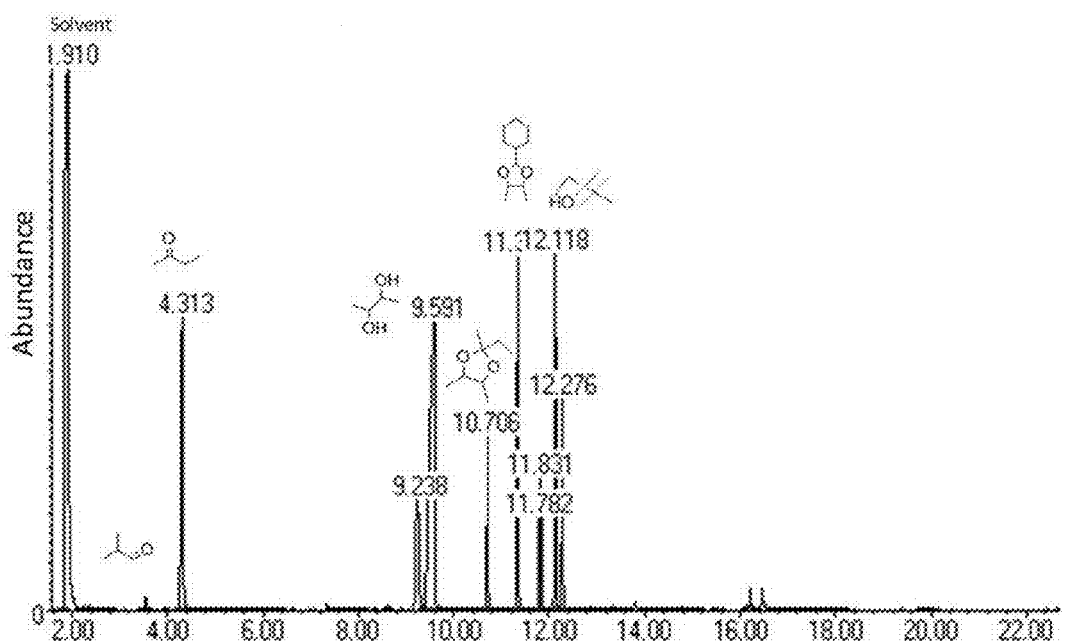
FIG. 2 is a gas chromatogram of products obtained when BDO and H-ZSM-5 (30) were heated to 300° C. for 4 hours in a Parr reactor.

H-ZSM-5 ($SiO_2$/$Al_2O_3$=30), 2 g, and 150 mL of BDO (Aldrich) were loaded into a 300 mL Parr reactor. The reactor was purged with N2 then heated to 300° C. for 4 h, reaching a final pressure of 1750 psig. The BDO conversion was 57% and the liquid products included 15.8% MEK, many aldol condensation products, the dioxolane ketal (product of BDO and MEK condensation) (FIG. 2), and many cracking products in the gaseous phase. The gas analysis showed about 30% propane, 9% butane, 11.5% butane, 1% pentene, 3% 1,2-dimethylcyclopropane, 11% IBA and 36.5% MEK.

Figure 3:
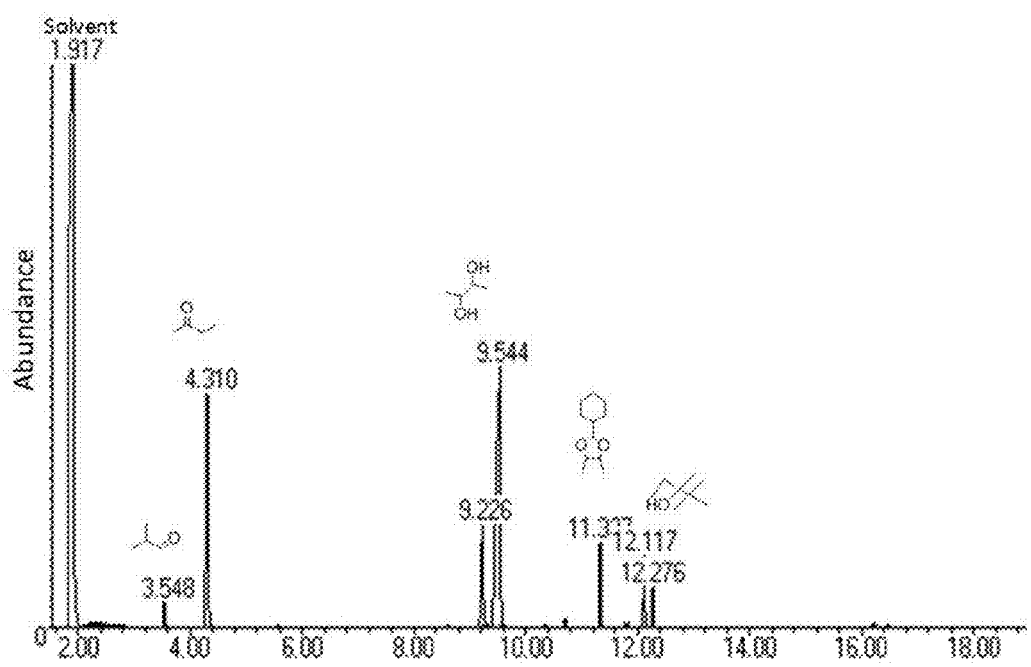
FIG. 3 is a gas chromatogram of products obtained after water was added to the Parr reactor containing the reaction mixture of FIG. 2, and the reaction mixture was heated for an additional hour at 300° C.

Water, 10 mL, was added to the products in the Parr reactor and heated to 300° C. for another hour (FIG. 3). Ketals were reduced in concentration, and the BDO and MEK in the solution phase increased to 61.6% and 23.8%, respectively, suggesting that the ketal was converted back to the starting material and MEK by hydrolysis.

Example 4

Conversion of BDO to MEK in a Continuous Flow Reactor

Initial runs were conducted with pure BDO rather than an aqueous BDO solution because it was thought that water would eventually deactivate the catalyst by dealumination. Selectivity to MEK in the anhydrous feed was found to be low, however, because condensation reactions were favored. Later runs used aqueous solutions of BDO, leading to much higher selectivities to MEK and IBA. Dealumination was minimized by use of an appropriate water concentration.

The flow reactor was loaded with 1.2 g of H-ZSM-5(30). Pure Aldrich BDO was used as feed with a feed rate of 0.05 mL/min and the reactor was heated to 300° C. Samples were collected over the 92 h time-on-stream (TOS) experiment and results are shown in Table 3.

TABLE 3

Conversion of BDO to MEK over H-ZSM-5(30) catalyst in the flow reactor at 300° C.

| Sample | TOS (h) | Color | MEK | IBA | Butadiene | Products BDO | Aromatics | Naphthalene | C8 |
|---|---|---|---|---|---|---|---|---|---|
| 1 | 3 | brown | 0.84 | 0 | — | — | 62 | 14.2 | 1.6 |
| 2 | 6 | brown | 23.9 | 5.2 | 2.1 | — | 31.9 | 1.9 | 6.9 |
| 3 | 17.5 | brown | 48.9 | 15.4 | 5.4 | — | — | — | 13.2 |
| 4 | 21.75 | brown | 57.1 | 17.8 | 4.1 | — | — | — | 5.5 |
| 5 | 25.5 | lt brown | — | — | — | — | — | — | — |
| 6 | 42 | yellow | 72 | 25 | — | — | — | — | — |
| 7 | 50 | yellow | 80 | 15 | — | — | — | — | — |
| 8 | 67.8 | yellow | — | — | — | — | — | — | — |
| 9 | 74 | yellow | 52 | 19.1 | — | 3 | — | — | — |
| 10 | 92 | lt yellow | — | — | — | — | — | — | — |

Figure 4:
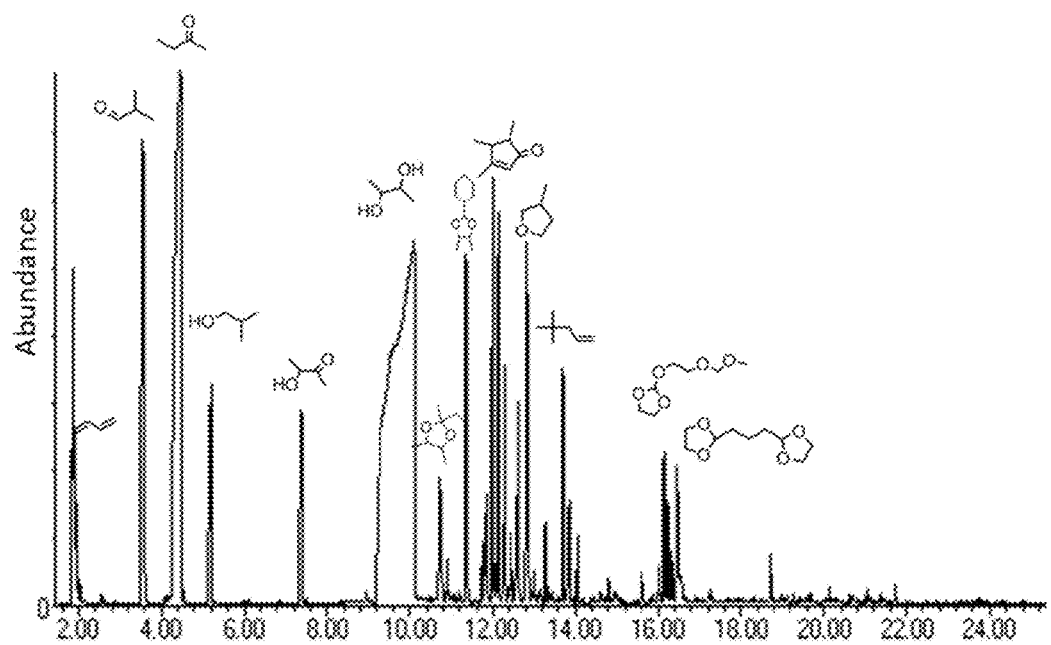
FIG. 4 is a gas chromatogram of products obtained when BDO was exposed to H-ZSM-5 (30) in a continuous flow reactor at 300° C.

Initially, the H-ZSM-5(30) was very active in producing aromatics. The catalyst also produced numerous condensation products (FIG. 4); C8 condensation products are shown in Table 3. However, the catalyst lost activity quickly and at 3 hours time-on-stream (TOS) the formation of aromatics ceased and MEK and isobutyraldehyde (IBA) became the dominant products. Condensation products might have promoted coke formation, but this could not be confirmed.

Figure 5:
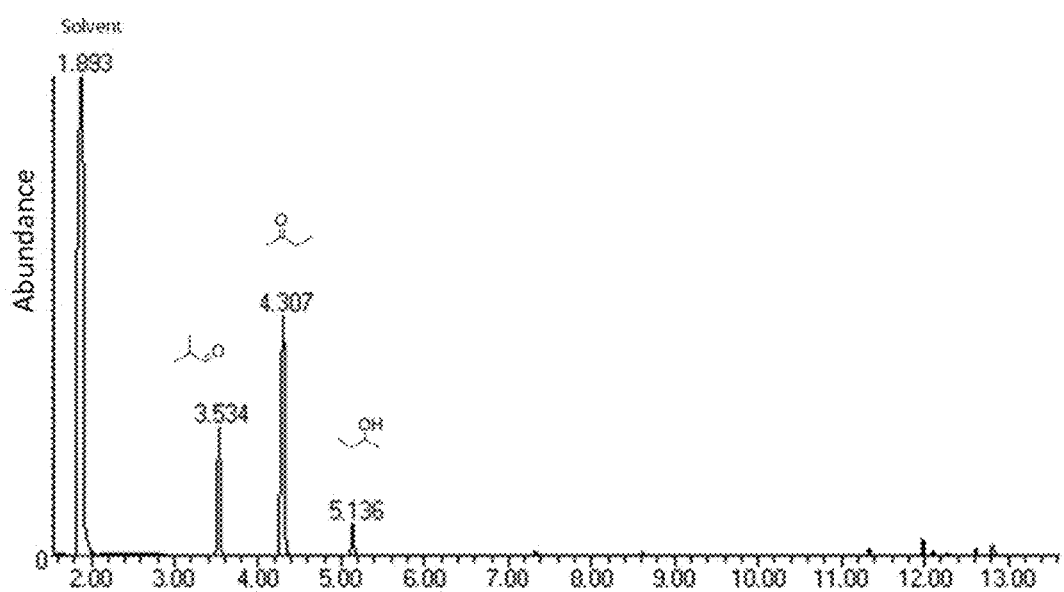
FIG. 5 is a gas chromatogram of products obtained when 50% BDO in water was exposed to H-ZSM-5 (30) in a continuous flow reactor at 300° C.

When the pure BDO was replaced with 50% BDO in water in the continuous reactor run, the MEK/IBA yield was improved and far fewer condensation by-products were formed (FIG. 5). Because of the large water concentration, however, the H-ZSM-5 catalyst deactivated over time. This deactivation was likely caused by dealumination of H-ZSM-5 (30) in water. An attempt to regenerate the catalyst by combustion in air (to remove coke) formed a material that could not produce aromatics, indicating the deactivation is permanent. (The performance of ZSM-type catalysts was later improved by adjusting the water concentration as discussed below.)

The effect of temperature on conversion and selectivity over alumina (Engelhard 4126) in the continuous flow reactor was evaluated using pure (Table 4) and aqueous (Table 5) BDO from LanzaTech and Aldrich. 1.5 g of Engelhard alumina was used as catalyst in each experiment. The $H_2$ pressure was 200 psig and the $H_2$ flow rate was 400 mL/min. The flow rate of pure LanzaTech or Aldrich BDO was 0.1 mL/min. When 50% BDO was used (from both LanzaTech and Aldrich), the flow rate was doubled to maintain the same space velocity of BDO in the reactor. Aqueous feeds often resulted in a 2-phase product, each phase being analyzed separately.

TABLE 4

The conversion of LanzaTech and Aldrich BDO (no added water) over alumina (Engelhard 4126)

| | LanzaTech BDO | | Aldrich BDO | |
|---|---|---|---|---|
| T (° C.) | MEK + IBA | BDO | MEK + IBA | BDO |
| 300 | 21.8 | 0 | 20.6 | 0 |
| 280 | 25.7 | 0 | 30.8 | 1.3 |
| 260 | 14 | 20.8 | 33 | 1.9 |
| 240 | 6.3 | 35.4 | 11.3 | 32 |
| 220 | 1.9 | 61.4 | 6.1 | 48.2 |
| 200 | 1.7 | 65.6 | 3 | 74 |

TABLE 5

The reaction of LanzaTech and Aldrich BDO (50% in water) with alumina (Engelhard 4126). The feed rate for BDO was doubled to keep the space velocity of BDO constant.

| | LanzaTech BDO | | | Aldrich BDO | |
|---|---|---|---|---|---|
| T (° C.) | MEK + IBA | dl-BDO | meso-BDO | MEK + IBA | BDO |
| 300 (org) | 37 | 0 | 0 | 34.8 | 0 |
| 300 (aq) | 36.2 | 21.6 | 1.6 | 56 | 3.8 |
| 280 (org) | 38.9 | 7 | 0 | 36.6 | 0 |
| 280 (aq) | 20.9 | 32.3 | 3.1 | 39 | 17.2 |
| 260 * | — | — | — | 19.4 | 32 |
| 240 * | — | — | — | 1.3 | 29.5 |
| 220 * | — | — | — | 0 | 30 |
| 200 * | — | — | — | 0 | 30 |

TABLE 5-continued

The reaction of LanzaTech and Aldrich BDO (50% in water) with alumina (Engelhard 4126). The feed rate for BDO was doubled to keep the space velocity of BDO constant.

| T (° C.) | LanzaTech BDO | | | Aldrich BDO | |
|---|---|---|---|---|---|
| | MEK + IBA | dl-BDO | meso-BDO | MEK + IBA | BDO |
| 160 * | — | — | — | 0 | 94 |
| 140 * | — | — | — | 0 | 94 |

* single phase product

Over alumina, the reactivity of BDO from either Lanza-Tech or Aldrich was similar. The conversion of BDO to MEK occurred above about 260° C. with highest conversions above 280° C. Like the results discussed above for H-ZSM-5 (30), the selectivity to MEK was higher in the presence of 50% water.

The effect of temperature on BDO conversion for feeds containing varying water concentration over a different H-ZSM-5 catalyst than used above, H-ZSM-5 (Si/Al=23), was examined in the continuous flow reactor. The primary objective was to determine temperatures giving highest conversions for the various feeds. Pure Aldrich BDO, Aldrich BDO containing 50 wt % water, and LanzaTech BDO containing 10 wt % water were tested. As in the alumina experiments, the $H_2$ pressure was 200 psig and the $H_2$ flow rate was 400 mL/min. The liquid feed rate was 0.1 mL/min for both pure and 50% aqueous BDO solutions. For the 90% aqueous BDO feed solution, a feed rate of 0.06 mL/min was used.

Pure Aldrich BDO (which is mostly the meso isomer) did not begin converting until about 240° C. (Table 6). Complete conversion was not attained, even at 300° C. For reference, H-ZSM-5(30) was found earlier to convert BDO completely at 300° C. (Table 3) indicating that the increased acidity as the Si/Al ratio decreases is important. Better conversion over H-ZSM-5(23) was observed for the 50% BDO feed (Table 7). In this case, conversion was nearly complete at 280° C., with about 2.9% BDO remaining, and complete at 300° C. The d/l isomer apparently converted more readily than the meso isomer as indicated by the d/l to meso ratio at each temperature. While not explicitly tested in this series of experiments, it was assumed that the catalyst deactivated with 50% water present as observed in the H-ZSM-5(30) experiments.

TABLE 6

The reaction of Aldrich BDO (no added water) over H-ZSM-5(23)

| T (° C.) | MEK + IBA | BDO |
|---|---|---|
| 300 | 26.5 | 21.2 |
| 280 | 22 | 42.6 |
| 260 | 11 | 56 |
| 240 | 4.9 | 78.3 |
| 220 | 0 | 90 |
| 200 | 0 | 94.5 |

TABLE 7

The reaction of Aldrich BDO (50% in water) over H-ZSM-5(23)

| T (° C.) | MEK + IBA | d/l-BDO | meso-BDO | (d/l)/(meso) ratio |
|---|---|---|---|---|
| 300 | 88.6 | 0 | 0 | — |
| 280 | 59.4 | 0 | 2.9 | — |
| 260 | 67.2 | 3 | 14.1 | 0.21 |
| 240 | 20.6 | 16.6 | 57.3 | 0.29 |
| 220 | 2 | 26.3 | 71.7 | 0.37 |
| 200 | 0 | 27.5 | 72.5 | 0.38 |

Catalyst longevity and activity were examined using 10% water/90% LanzaTech BDO. Activity remained high throughout the 120.5 h (5 days) experiment (Table 8). Compositions of both the organic and aqueous phases were determined. Conversion of both d/l and meso isomers was complete at 300° C. Dropping the temperature briefly to 280 then 260° C. resulted in decreased conversion, but raising it again to 300° C. resumed the previous activity.

TABLE 8

The reaction of LanzaTech BDO (90% in water) over H-ZSM-5(23); flow rate = 0.06 mL/min

| Time (hr) | T (° C.) | MEK + IBA | d/l-BDO | meso-BDO |
|---|---|---|---|---|
| 2 (org) | 300 | 32 | 1.8 | 0 |
| 2 (aq) | 300 | 24.3 | 62.9 | 6.5 |
| 5 (org) | 300 | 59.9 | 0 | 0 |
| 5 (aq) | 300 | 68.5 | 0 | 0 |
| 13 (org) | 300 | 60.5 | 0 | 0 |
| 13 (aq) | 300 | 74.6 | 2.1 | 0 |
| 18 (org) | 300 | 57.7 | 0 | 0 |
| 18 (aq) | 300 | 70.6 | 0 | 0 |
| 20 (org) | 300 | 62.2 | 1.8 | 0 |
| 20 (aq) | 300 | 69.5 | 0 | 0 |
| 21.5 (org) | 300 | 60.7 | 0 | 0 |
| 21.5 (aq) | 300 | 70 | 0 | 0 |
| 24 (org) | 300 | 61 | 0 | 0 |
| 24 (aq) | 300 | 69.4 | 0 | 0 |
| 27 (org) | 300 | 63.3 | 0 | 0 |
| 27 (aq) | 300 | 64 | 2.7 | 5.3 |
| 40 (org) | 300 | 63.4 | 0 | 0 |
| 40 (aq) | 300 | 66.6 | 0 | 0 |
| 43 (org) | 300 | 62.3 | 0 | 0 |
| 43 (aq) | 300 | 66.9 | 0.7 | 1.3 |
| 44 (org) | 300 | 62 | 0 | 0 |
| 44 (aq) | 300 | 67 | 0.1 | 0.1 |
| 45.5 (org) | 300 | 63.2 | 0 | 0 |
| 45.5 (aq) | 300 | 68 | 0.1 | 0.1 |
| 48 (org) | 300 | 65 | 0 | 0 |
| 48 (aq) | 300 | 60.7 | 2.5 | 0.7 |
| 49.5 (org) | 300 | 65 | 0 | 0 |
| 49.5 (aq) | 300 | 56.2 | 5.9 | 0.6 |
| 50.5 (org) | 280 | 31.6 | 39.5 | 1.7 |
| 52 (org) | 260 | 22.4 | 45.5 | 2.2 |
| 61.5 (org) | 300 | 62.4 | 0 | 0 |
| 61.5 (aq) | 300 | 55 | 17.3 | 1 |
| 71 (org) | 300 | 63.7 | 0 | 0 |
| 71 (aq) | 300 | 78.4 | 0.9 | 0 |
| 76.5 (org) | 300 | 62 | 0 | 0 |
| 76.5 (aq) | 300 | 66.2 | 0 | 0 |
| 86.5 (org) | 300 | 64.9 | 0 | 0 |
| 86.5 (aq) | 300 | 67 | 0 | 0 |
| 99.5 (org) | 300 | 64.9 | 0 | 0 |
| 99.5 (aq) | 300 | 63.9 | 0 | 0 |
| 112.5 (org) | 300 | 64.5 | 0 | 0 |
| 112.4 (aq) | 300 | 64.4 | 0 | 0 |
| 120.5 (org) | 300 | 62.5 | 0 | 0 |
| 120.5 (aq) | 300 | 64.5 | 0 | 0 |

Figure 6:
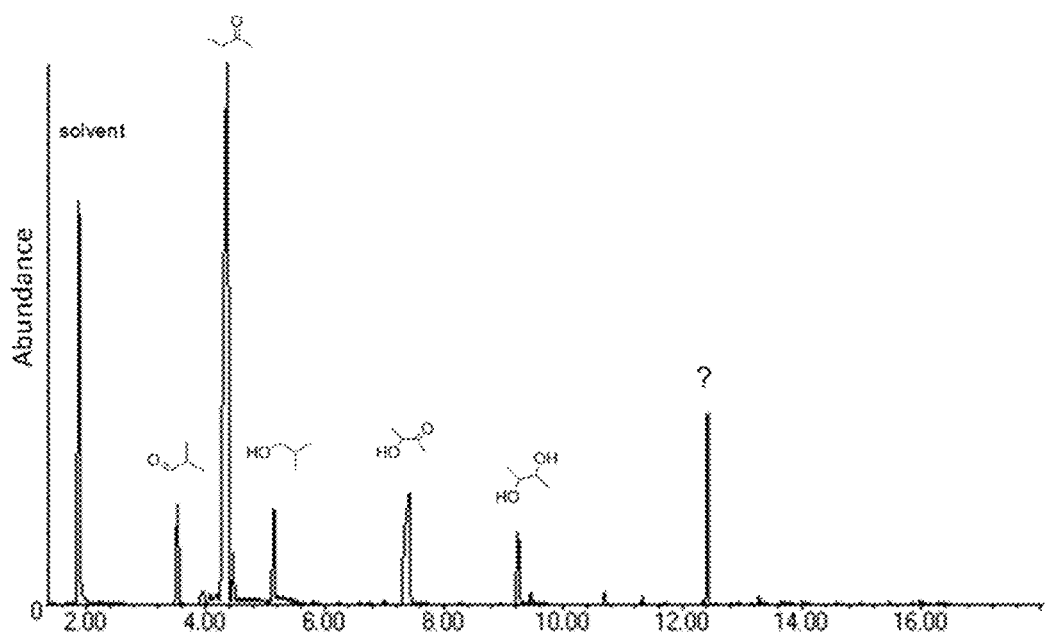
FIG. 6 is a gas chromatogram of combined aqueous phases of samples taken from 61.5 h to 120.5 h in a continuous conversion of LanzaTech BDO to MEK over H-ZSM-5 (23) at 300° C.
Figure 7:
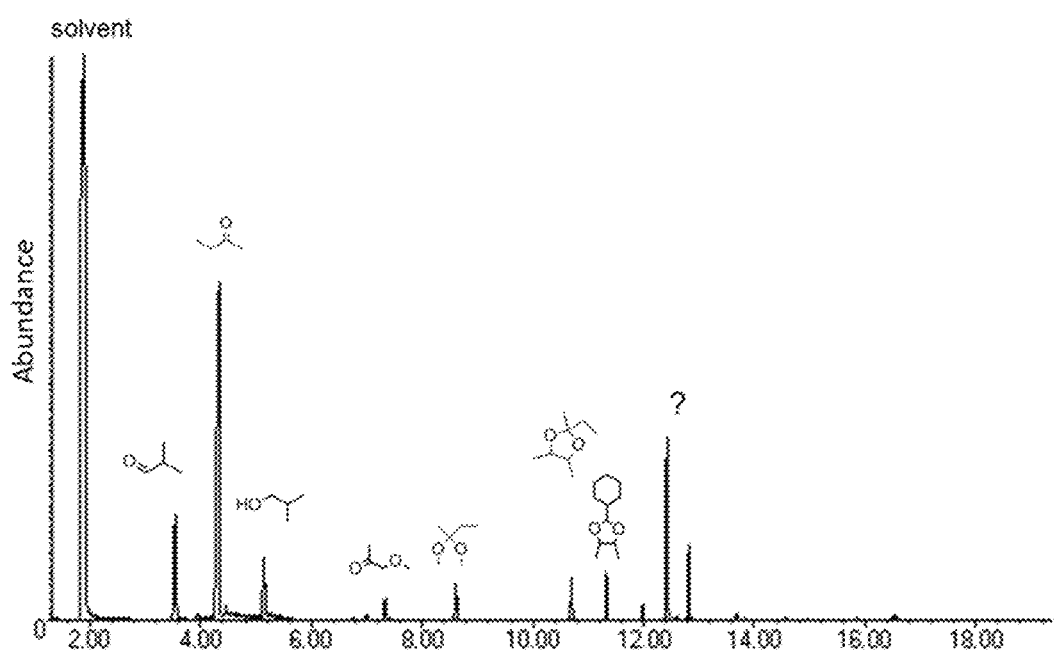
FIG. 7 is a gas chromatogram of combined organic phases of samples taken from 61.5 h to 120.5 h in a continuous conversion of LanzaTech BDO to MEK over H-ZSM-5 (23) at 300° C.

The samples from 61.5 to 120.5 h were combined and the organic and liquid phases separated. The GC's of the aqueous and organic phases are shown in FIGS. 6 and 7, respectively. Note that remaining BDO partitions to the aqueous phase, ketals partition to the organic phase, IBA is found in both phases, and both reduced (isobutanol) and oxidized (3-hydroxy-2-butanone, and others) products were formed. An unidentified material for which no reasonable matches were obtained in the MS eluted at about 12.5 minutes. Peak identification in these and following figures is based on best matches with the MS library and has not necessarily been confirmed with standards. The presence of the dimethyl ketal product requires verification, but the diluting solvent used for these samples was methanol and it may be possible this product was formed during sample preparation Example 5

Hydrogenation of MEK to 2-Butanol in a Parr Reactor

The hydrogenation catalyst used for the batch reduction was 5% Ru/C (ESCAT 440, Engelhard Lot C5070 CHO1114). 5 g of Ru/C was loaded into a 300 mL Parr reactor with 100 mL MEK. The reactor was purged 3 times with $H_2$. It was then filled with 800 psig $H_2$. The reactor was heated to 100° C. and the stir rate was set to 300 rpm. The $H_2$ uptake happened quickly, stopping after 25 minutes. The yield of 2-butanol was over 95%.

Example 6

Figure 8:
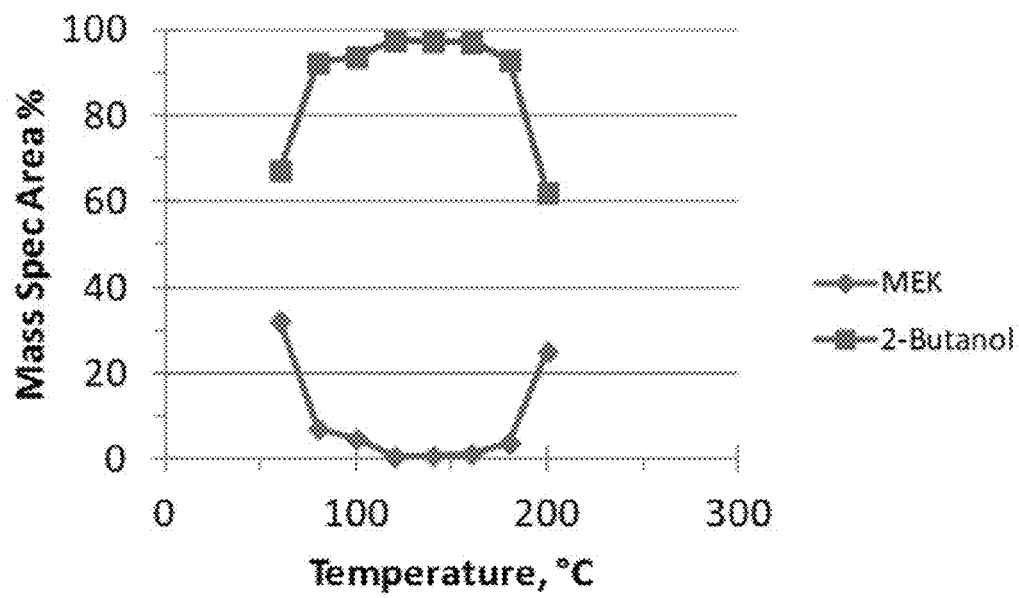
FIG. 8 is a graph illustrating the effect of temperature on MEK hydrogenation to 2-butanol over 5% Ru/C at 200 psig $H_2$.

Hydrogenation of MEK to 2-Butanol in a Continuous Flow Reactor 1.5 g of 5% Ru/C (ESCAT 440, Lot C5070 CHO1114) was loaded into the flow reactor. The reactor was charged with 200 psig $H_2$ and a $H_2$ flow rate of 400 mL/min was used. A variety of temperatures between 60 and 200° C. were examined with a MEK feed rate of 0.1 mL/min. The results, shown in Table 9 and FIG. 8, are consistent with the reaction being kinetically limited at 60° C., but equilibrium limited at 200° C. Temperatures between 120 and 160° C. gave the best yields. Pressures higher than 200 psig would tend to further increase 2-butanol formation.

TABLE 9

Effect of temperature on 2-butanol selectivity in MEK reduction with 5% Ru/C catalyst at 200 psig $H_2$

| T (° C.) | MEK | 2-Butanol |
|---|---|---|
| 200 | 25.2 | 62.1 |
| 180 | 3.9 | 92.9 |
| 160 | 1.4 | 97.1 |
| 140 | 0.87 | 97.3 |
| 120 | 0.65 | 97.5 |
| 100 | 4.8 | 93.7 |
| 80 | 7.2 | 92.3 |
| 60 | 32.2 | 67.3 |

Figure 9:
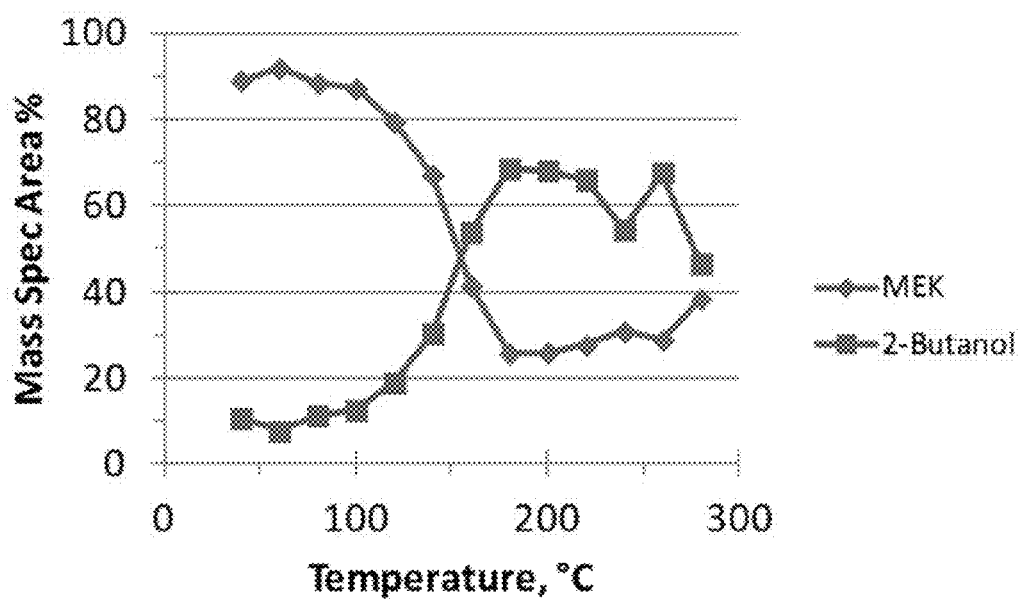
FIG. 9 is a graph illustrating the effect of temperature on MEK hydrogenation to 2-butanol over 5% Pt/C at 200 psig $H_2$.

1.5 g of 5% Pt/C (ESCAT238, Lot C5018 CHO1172) was loaded into the flow reactor. The reactor was pressurized to 200 psig with $H_2$. The $H_2$ flow rate during the experiment was 400 mL/min. Reaction temperatures between 40 and 280° C. were studied with a MEK feed rate of 0.1 mL/min. Samples were collected at each temperature (Table 10 and FIG. 9). With 5% Pt/C, the equilibrium concentration of 2-butanol at 68% is lower than for 5% Ru/C. Again, higher pressures of $H_2$ would be required to shift the equilibrium toward the reduced product.

TABLE 10

Effect of temperature on alcohol selectivity in MEK reduction with 5% Pt/C catalyst at 200 psig $H_2$

| T (° C.) | MEK | 2-butanol |
|---|---|---|
| 280 | 38.4 | 46.5 |
| 260 | 28.8 | 67.7 |
| 240 | 30.8 | 54.4 |
| 220 | 27.6 | 66 |
| 200 | 25.9 | 68.1 |
| 180 | 25.8 | 68.5 |
| 160 | 41.4 | 53.9 |
| 140 | 67.1 | 30.4 |
| 120 | 79.3 | 18.9 |
| 100 | 87.1 | 12.6 |
| 80 | 88.4 | 11.4 |
| 60 | 91.8 | 7.8 |
| 40 | 89 | 10.8 |

Figure 10:
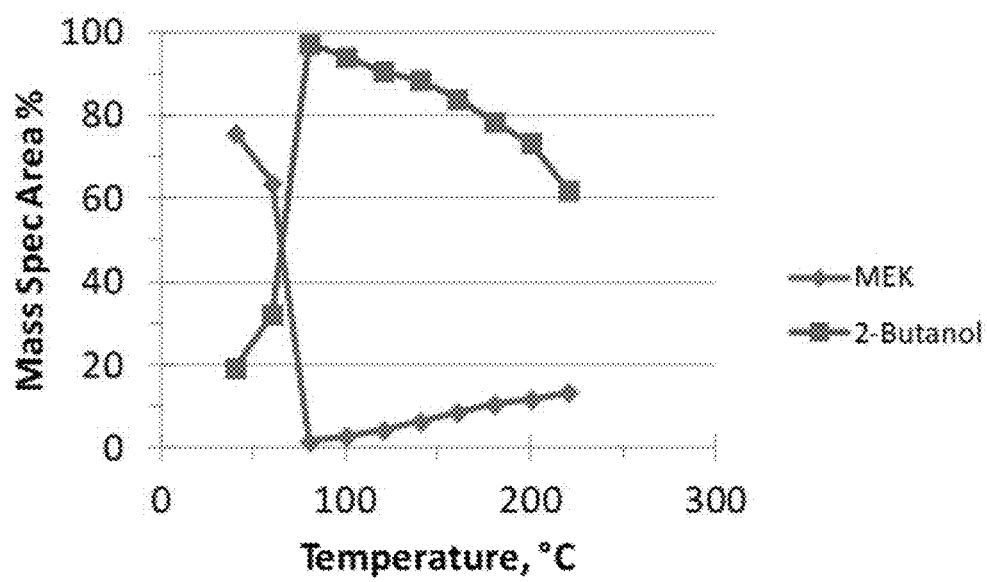
FIG. 10 is a graph illustrating the effect of temperature on MEK hydrogenation to 2-butanol over Raney Ni at 200 psig $H_2$.

The process was repeated using 1.5 g of Raney Ni as catalyst in the continuous flow reactor. The reactor was pressurized to 200 psig with $H_2$ and same flow rate of 400 mL/min was used. Temperatures between 40 and 220° C. were studied. The MEK feed rate was 0.1 mL/min. Solution compositions at each temperature are shown in Table 11 and FIG. 10. The best results were obtained at 80° to 100° C.

TABLE 11

Effect of temperature on alcohol selectivity in MEK reduction with Raney Ni catalyst at 200 psig $H_2$

| T (° C.) | MEK | 2-Butanol |
|---|---|---|
| 220 | 13.5 | 62 |
| 200 | 11.8 | 73.4 |
| 180 | 10.6 | 78.5 |
| 160 | 8.7 | 83.9 |
| 140 | 6.4 | 88.5 |
| 120 | 4.4 | 90.6 |
| 100 | 3 | 94 |
| 80 | 1.6 | 97.2 |
| 60 | 63.7 | 32.2 |
| 40 | 75.7 | 19.3 |

Figure 11:
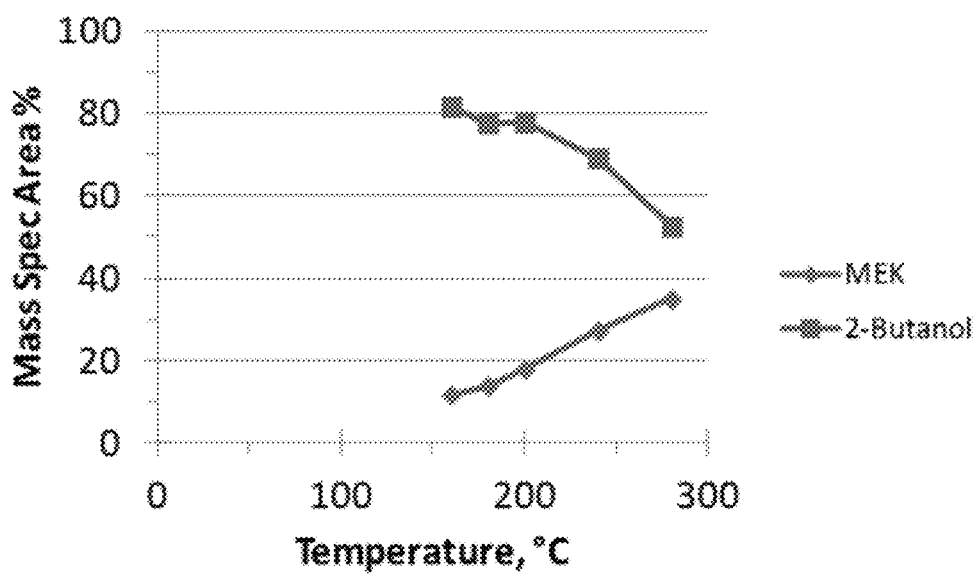
FIG. 11 is a graph illustrating the effect of temperature on MEK hydrogenation to 2-butanol over 2.5% Re/2.5% Ni/C at 180-200 psig $H_2$.
Figure 12:
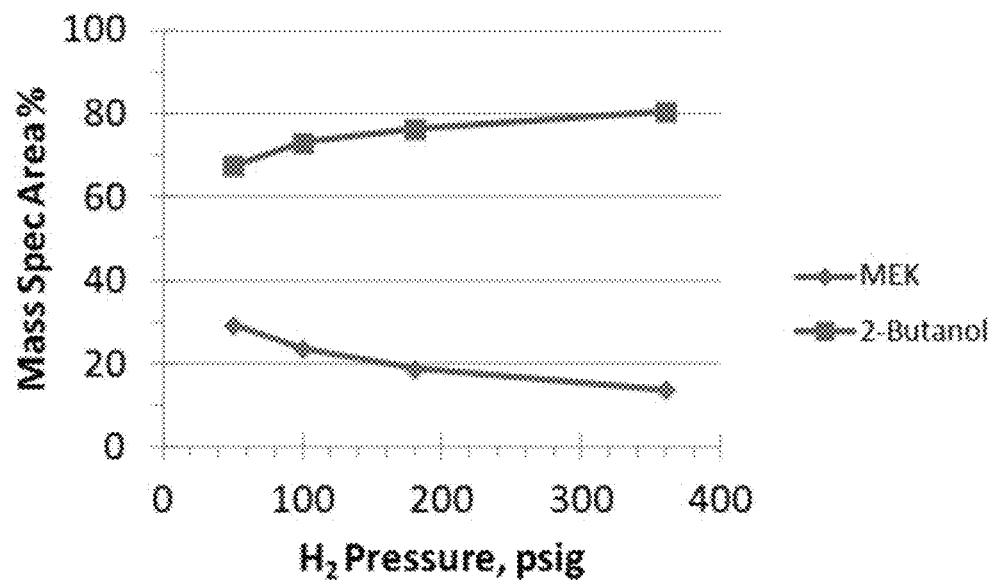
FIG. 12 is a graph illustrating the effect of pressure on MEK hydrogenation to 2-butanol over 2.5% Re/2.5% Ni/C at 220° C.

The hydrogenation of MEK to 2-butanol with Re/Ni/C catalyst (Engelhard 6818-18-1, 2.5% Re and 2.5% Ni, activated at 280° C. overnight) was also conducted in the continuous flow reactor. 1.5 g of Re/Ni/C was loaded into the flow reactor. The reactor was fed with 200 psig of $H_2$ at a flow rate of 400 mL/min. The experiment was conducted between 160 and 280° C. The MEK feed rate was 0.05 mL/min, or half the rate as in the previously discussed cases. Results are shown in Table 12, FIG. 11, and FIG. 12. Hydrogenation is more favorable at lower temperature (FIG. 11) and higher hydrogen pressure (FIG. 12).

TABLE 12

Effect of temperature on alcohol selectivity in MEK reduction with Re/Ni/C catalyst at various $H_2$ pressures

| T (° C.) | Pressure | MEK | 2-butanol |
|---|---|---|---|
| 280 | 200-180 | 35 | 52.6 |
| 240 | 200-180 | 27.3 | 69.2 |
| 200 | 200-180 | 18 | 77.8 |
| 180 | 200-180 | 14 | 77.6 |
| 160 | 200-180 | 11.8 | 81.7 |
| 220 | 390-360 | 13.9 | 80.5 |
| 220 | 200-180 | 18.8 | 76.3 |

TABLE 12-continued

Effect of temperature on alcohol selectivity in MEK reduction
with Re/Ni/C catalyst at various $H_2$ pressures

| T (° C.) | Pressure | MEK | 2-butanol |
|---|---|---|---|
| 220 | 120-100 | 23.8 | 73 |
| 220 | 60-50 | 29.4 | 67.6 |

Figure 13:
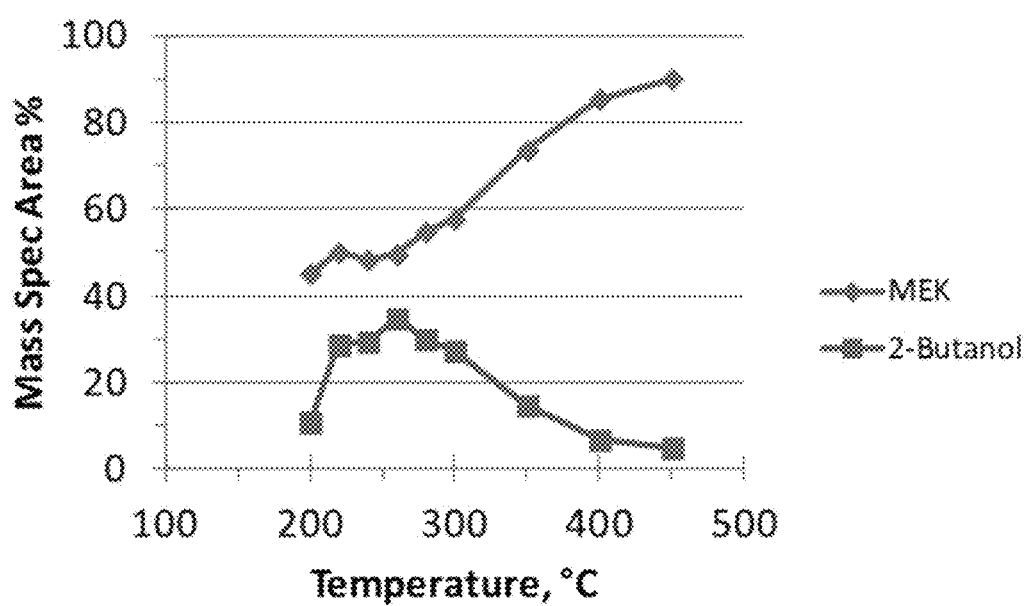
FIG. 13 is a graph illustrating the effect of temperature on MEK hydrogenation to 2-butanol over 1.5% Pd/C at 200 psig $H_2$.

1.5% Pd/C catalyst (Engelhard) was examined for hydrogenation of MEK to 2-butanol in the continuous flow reactor. 1.5 g of Pd/C was loaded into the flow reactor. The reactor was fed with 200 psig of $H_2$ and run at a $H_2$ flow rate of 400 mL/min at temperatures between 200 and 450° C. The MEK feed rate was 0.1 mL/min. Results are shown in Table 13 and FIG. 13. The optimal temperature at 200 psig is about 260° C., but the equilibrium concentration is only about 35%.

TABLE 13

Effect of temperature on alcohol selectivity in MEK reduction
with 1.5% Pd/C catalyst

| T (° C.) | MEK | 2-Butanol |
|---|---|---|
| 450 | +90 | <5 |
| 400 | 85.4 | 6.8 |
| 350 | 73.5 | 14.8 |
| 300 | 57.7 | 27.3 |
| 280 | 54.8 | 30 |
| 260 | 49.6 | 34.8 |
| 240 | 48.3 | 29.4 |
| 220 | 50 | 28.7 |
| 200 | 45.2 | 10.9 |

Figure 14:
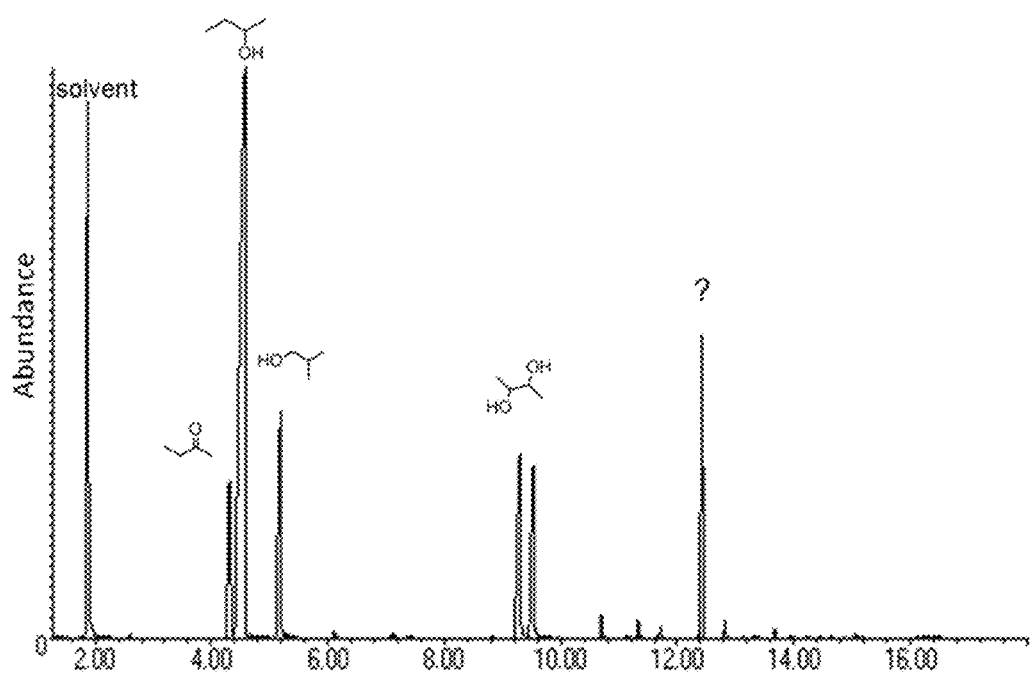
FIG. 14 is a gas chromatogram of reduction products formed over 5% Ru/C at 160° C. using as feed the combined aqueous samples collected between 61.5 to 120.5 h in the conversion of LanzaTech BDO to MEK over H-ZSM-5(23).
Figure 15:
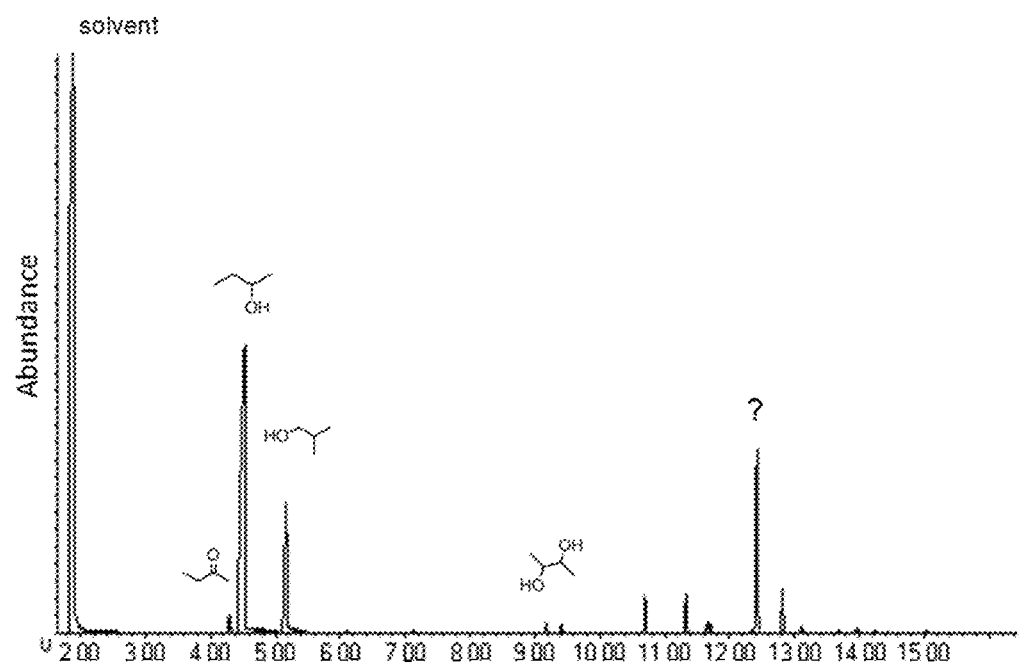
FIG. 15 is a gas chromatogram of reduction products formed over 5% Ru/C at 160° C. using as feed the combined organic samples collected between 61.5 to 120.5 h in the conversion of LanzaTech BDO to MEK over H-ZSM-5(23).

The samples collected from 61.5 to 120.5 h in the reaction of LanzaTech BDO (90% in water) over H-ZSM-5(23) (Example 4, Table 8) were combined and the organic and liquid phases separated. These phases were separately hydrogenated to 2-butanol. The 5% Ru/C (Engelhard) catalyst (1.5 g) was tested for MEK reduction (MEK feed rate=0.05 mL/min, $H_2$ feed rate=400 mL/min, 200 psig and 160° C.) in the continuous flow reactor. The results for hydrogenation of the aqueous phase are shown in Table 14 and FIG. 14, while those for the organic phase are shown in Table 15 and FIG. 15. In both cases, the combined 2-butanol+isobutanol yield was over 95%. In addition, hydrogenation of aqueous MEK samples collected in the BDO to MEK reactor between 2 and 45.5 h (Table 8) showed similar results with over 98% combined yield of these alcohols being obtained. Ketals were apparently split to BDO and MEK with the MEK being hydrogenated to 2-butanol. The unknown eluting at 12.5 min was unaffected by hydrogenation.

TABLE 14

Hydrogenation of the combined aqueous phases from the 61.5-120.5 h
samples from the BDO to MEK run in Table 8 with 5% Ru/C catalyst
in the flow reactor at 160° C.

| TOS (h) | MEK | IBA | 2-Butanol | Isobutanol | d/l-BDO | meso-BDO | % Reduction |
|---|---|---|---|---|---|---|---|
| 0 (feed) | 56.7 | 6.4 | 1.9 | 4.9 | 14.1 | 4.9 | 9.7 |
| 1 | 7.9 | | 52.9 | 8.3 | 18.7 | | 88.6 |
| 3 | 2.6 | | 54.5 | 7.9 | 26.4 | | 96.0 |

% Reduction = 100 × (2-Butanol + Isobutanol)/(MEK + IBA + 2-Butanol + Isobutanol)

TABLE 15

Hydrogenation of the combined organic phases from the
61.5-120.5 h samples from the BDO to MEK run in Table 8
with 5% Ru/C catalyst in the flow reactor at 160° C.

| TOS (h) | MEK | IBA | 2-Butanol | Isobutanol | % Reduction |
|---|---|---|---|---|---|
| 0 (feed) | 47.7 | 11.4 | 1 | 5.3 | 0 |
| 1 | 14.6 | 0 | 44.7 | 14.8 | 80.3 |
| 5.5 | 5.8 | 0 | 49 | 13.7 | 91.5 |
| 12.5 | 1.7 | 0 | 55 | 14.9 | 97.6 |
| 15.5 | 2.7 | 0 | 52 | 14.6 | 96.1 |

% Reduction = 100 × (2-Butanol + Isobutanol)/(MEK + IBA + 2-Butanol + Isobutanol)

Example 7

Integrated Step-Wise Conversion of BDO to 2-Butanol

In the above examples it was demonstrated that BDO can be converted to a product rich in MEK and that MEK can be converted to 2-butanol with a hydrogenation catalyst. Here, the results of testing with a combination of those two processes without intermediate separation are reported, demonstrating the direct conversion of BDO to 2-butanol in a flow reactor. The reactor consisted of two stages. In the first stage, feed BDO was converted to primarily MEK. The output of Stage 1 was fed directly to Stage 2, in which the MEK-rich product was hydrogenated to 2-butanol.

In the first stage, a tube was loaded with 2.79 g of H-ZSM-5 (23)/$Al_2O_3$. The tube was heated to 300° C. for BDO dehydration. The tube comprising the second stage was loaded with 0.55 g of Ru/C (Engelhard) catalyst. The Ru/C catalyst was heated to 275° C. in $H_2$ (200 psig) for one hour to activate the catalyst prior to use. The second stage was heated to 160° C. during conversion experiments. LanzaTech BDO containing 10% water was used as the feed with a flow rate of 0.1 mL/min into the first stage. The $H_2$ flow rate was at 400 mL/min and the reactor pressure was 200 psig. The reactor performance was checked by sampling after each stage.

Figure 16:
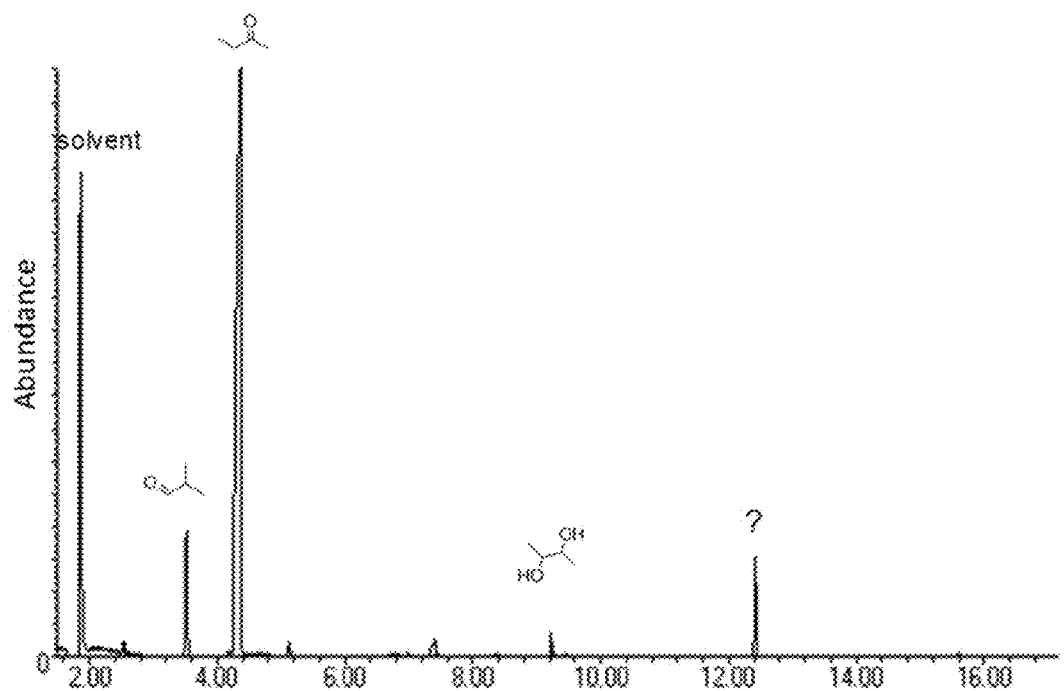
FIG. 16 is a gas chromatogram of products in an aqueous-phase sample taken at the outlet of the first stage of a combined reactor for an integrated step-wise conversion of BDO to 2-butanol.
Figure 17:
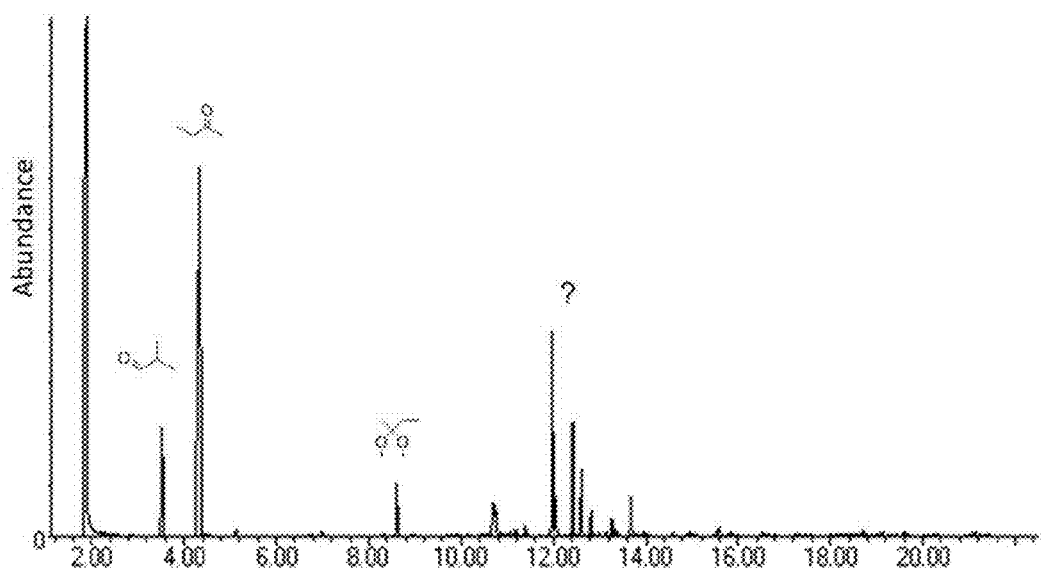
FIG. 17 is a gas chromatogram of products in an organic-phase sample taken at the outlet of the first stage of a combined reactor for an integrated step-wise conversion of BDO to 2-butanol.

The first stage used the H-ZSM-5(23) catalyst. Two samples were collected at the outlet of the first stage at the end of 2 and 3 hours. The analyses for organic and aqueous phases are listed below (Table 16) and GC traces are shown in FIGS. 16 and 17. BDO was nearly completely converted to a mixture of primarily MEK and IBA.

TABLE 16

First stage product-conversion of BDO to MEK
with H-ZSM-5 (23) catalyst

| TOS (h) | T (° C.) | BDO | MEK | IBA |
|---|---|---|---|---|
| 2 (org) | 300 | 0 | 44.9 | 6.4 |
| 2 (aq) | 300 | 7.6 | 77.2 | 5.8 |
| 3 (org) | 300 | | 45 | 8.4 |
| 3 (aq) | 300 | 1.3 | 74.5 | 7.4 |

Figure 18:
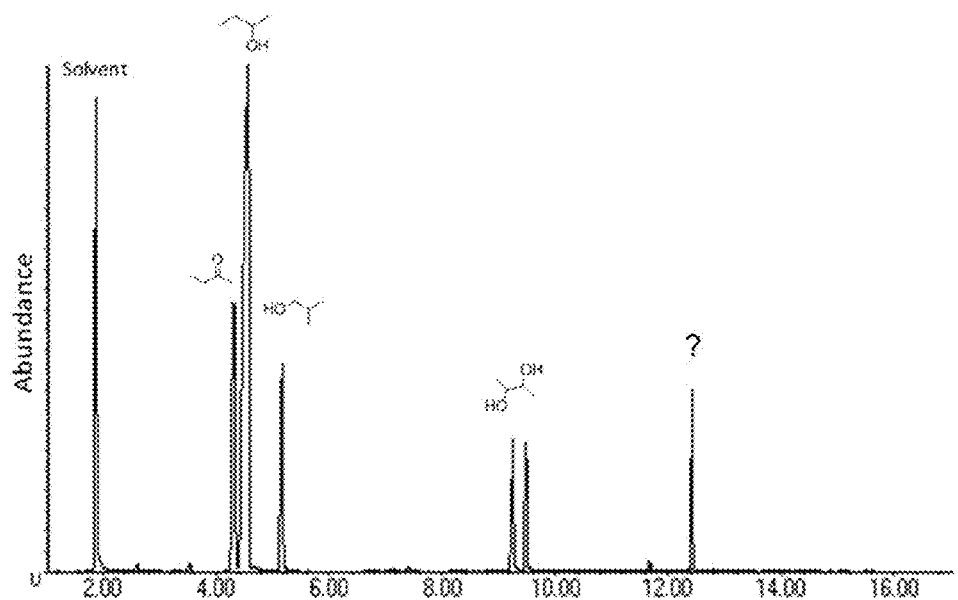
FIG. 18 is a gas chromatogram of products in an aqueous-phase sample taken at the outlet of the second stage of a combined reactor for an integrated step-wise conversion of BDO to 2-butanol.
Figure 19:
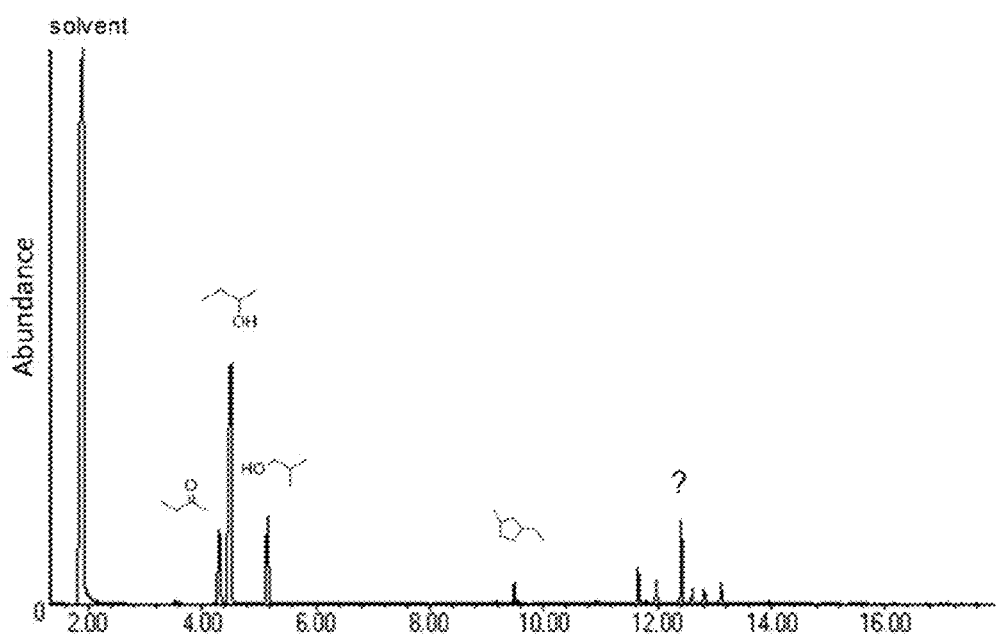
FIG. 19 is a gas chromatogram of products in an organic-phase sample taken at the outlet of the second stage of a combined reactor for an integrated step-wise conversion of BDO to 2-butanol.

One sample was collected from the exit of the second stage after 2 hours and analyzed with GC/MS (Table 17, FIG. 18, and FIG. 19). IBA was completely converted to isobutanol and MEK was converted to 2-butanol in about 80% yield. Unconverted BDO remained primarily in the aqueous phase. Higher yields of 2-butanol should be attainable by more completely activating the Ru/C catalyst (or by using a different catalyst) and by adjusting the residence time in Stage 2. A higher overall conversion of BDO to 2-butanol could be attained by adjusting the residence time in Stage 1 as well. Such optimization would improve the performance of the reactor. Nevertheless, this experiment demonstrates the direct conversion of BDO to 2-butanol in high yield. A third stage could easily be added to convert the 2-butanol to fuels or butenes.

TABLE 17

Sample taken from the second stage of the combined two stage conversion of BDO to 2-butanol (1st stage: H-ZSM-5(23) run at 300° C.; 2nd stage: 5%Ru/C run at 160° C.)

| Time (h) | MEK | IBA | 2-Butanol | Isobutanol | BDO |
|---|---|---|---|---|---|
| 2 (org) | 10 | 0 | 47 | 6.9 | 0.52 |
| 2 (aq) | 15.7 | 0 | 53.3 | 11.8 | 10.4 |

Example 8

Conversion of 2-Butanol to Hydrocarbons

Figure 20:
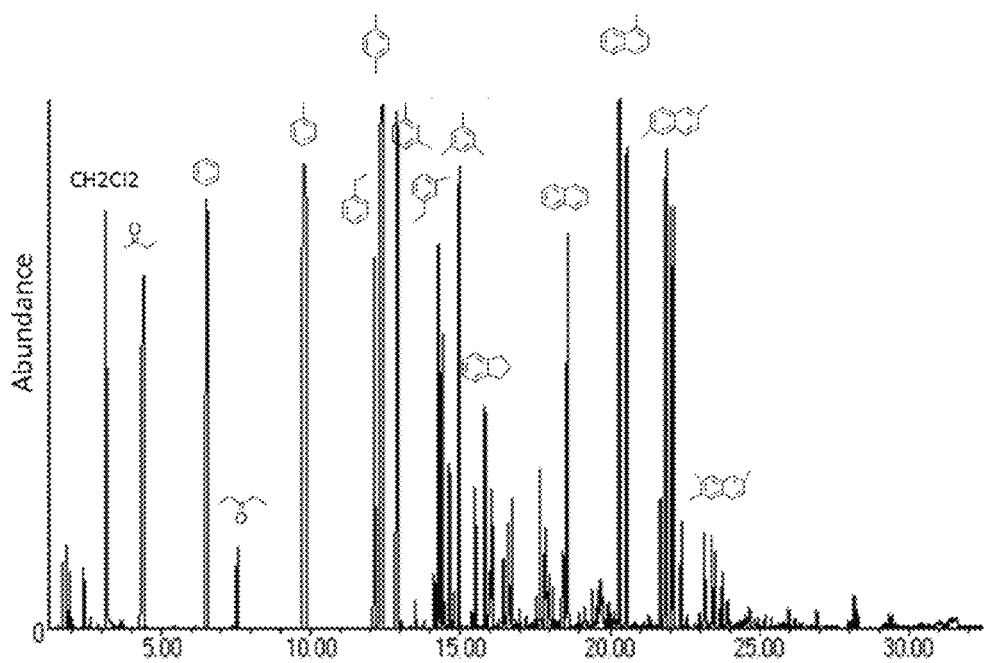
FIG. 20 is a gas chromatogram of products obtained from conversion of 2-butanol to hydrocarbons over H-ZSM-5(30) at 400° C.

The conversion of 2-butanol to hydrocarbons was demonstrated over H-ZSM-5(30) catalyst ($Al_2O_3$ binder) at 400, 300, and 250° C. in the flow reactor. Typically, 1.2 g catalyst was used with a 2-butanol feed rate of 0.05 mL/min. The liquid product is a 2-phase mixture of hydrocarbons (top) and water (bottom). Results obtained at 400° C. are shown in Table 18. Aromatics are formed at this temperature, and the catalyst had a much longer lifetime (>103 h) than when BDO or MEK were used as feeds (about 3 h). Performance appeared to be very stable over the course of the run with no apparent deactivation. A typical GC trace is shown in FIG. 20.

TABLE 18

Conversion of 2-butanol to hydrocarbons over H-ZSM-5(30)/$Al_2O_3$ catalyst at 400° C.

| Conditions/ Selected Products | Sample # | | | | |
|---|---|---|---|---|---|
| | 1 | 2 | 3 | 5 | 11 |
| Time (h) | 3.2 | 5.2 | 15 | 24.7 | 103 |
| T (° C.) | 400 | 400 | 400 | 400 | 450 |
| MEK | 6.3 | 1.1 | 0.4 | 0 | 0 |
| Benzene | 5.8 | 5.3 | 5.1 | 4.7 | 1.6 |
| Toluene | 11.2 | 11.5 | 11.4 | 11.3 | 7.1 |
| Di-trimethyl-benzene | 29.9 | 36 | 39.6 | 45 | 41.5 |

Figure 21:
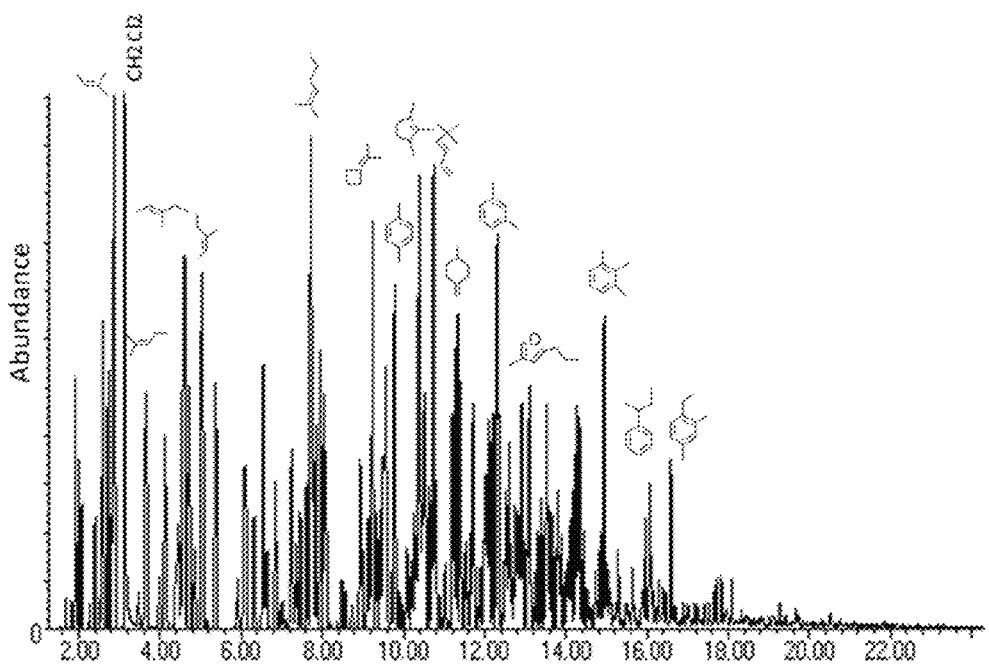
FIG. 21 is a gas chromatogram of products obtained from conversion of 2-butanol to hydrocarbons over H-ZSM-5(30) at 300° C.
Figure 22:
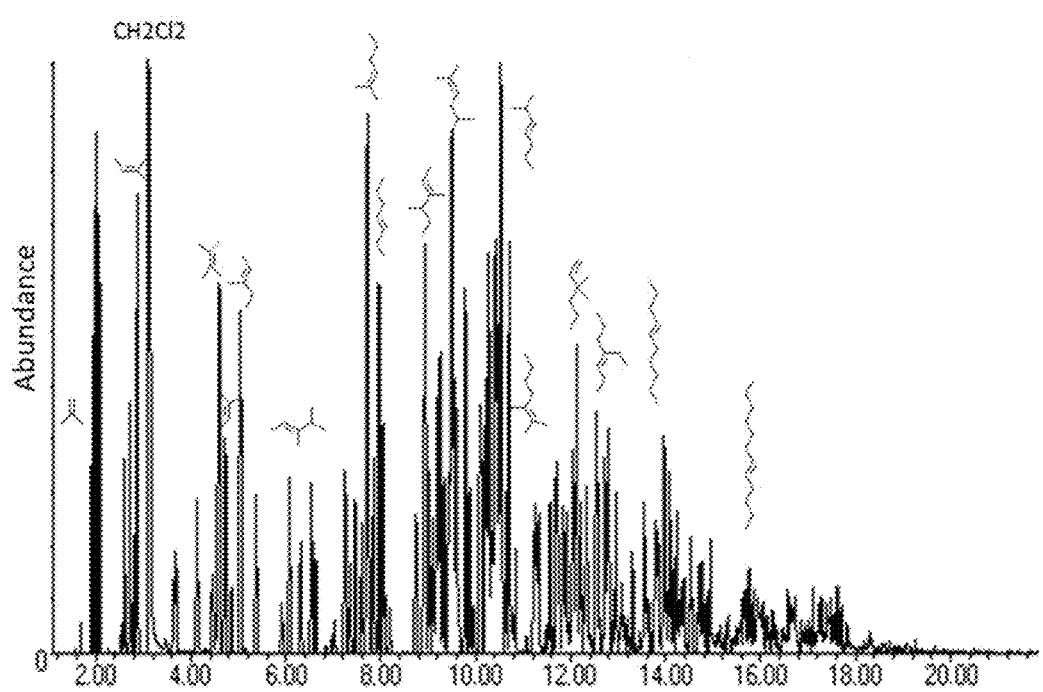
FIG. 22 is a gas chromatogram of products obtained from conversion of 2-butanol to hydrocarbons over H-ZSM-5(30) at 250° C.

Decreasing the reactor temperature changed the product composition. At 300° C. the hydrocarbon fraction was made up of a mixture of aromatics and normal and branched olefins (FIG. 21). Decreasing the temperature further to 250° C. gave a hydrocarbon product consisting of normal and branched C5→C12 olefins with almost no aromatic content (FIG. 22). This fraction could be hydrotreated to provide a mixture of paraffins and isoparaffins as a blend stock for jet fuel.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A method, comprising:
 converting 2,3-butanediol to 2-butanol by
  exposing a composition comprising aqueous 2,3-butanediol to an acidic catalyst to produce an intermediate composition comprising methyl ethyl ketone, and
  subsequently exposing the intermediate composition to a hydrogenation catalyst to produce a composition comprising 2-butanol, wherein the hydrogenation catalyst is spatially separated from the acidic catalyst.
2. The method of claim 1, wherein the composition comprises 50-95 wt % 2,3-butanediol.
3. The method of claim 1, wherein the acidic catalyst is a solid acid catalyst.
4. The method of claim 1, wherein the acidic catalyst comprises an H-ZSM-5 zeolite, an amorphous silicoaluminate, alumina, niobic acid, or a combination thereof.
5. The method of claim 1, wherein the composition is exposed to the acidic catalyst at a temperature within a range of 150° C. to 500° C. and/or at a pressure within a range of 10 psig to 1200 psig.
6. The method of claim 1, wherein the hydrogenation catalyst comprises Ru/C, Raney nickel, Re/Ni/C, Pt/C, or a combination thereof.
7. The method of claim 1, wherein the intermediate composition is exposed to the hydrogenation catalyst at a temperature within a range of 60° C. to 300° C. and/or a pressure within a range of 10 psig to 1200 psig.
8. The method of claim 1, further comprising:
 subsequently exposing the composition comprising 2-butanol to a deoxygenation catalyst; and
 deoxygenating the 2-butanol to produce hydrocarbons.
9. The method of claim 8, wherein the deoxygenation catalyst comprises a solid acid catalyst.
10. The method of claim 8, wherein:
 the 2-butanol is exposed to the deoxygenation catalyst at a temperature within a range of 200° C. to 275° C., and the hydrocarbons comprise unbranched C4-C12 olefins, branched C4-C12 olefins, or a combination thereof;
 the 2-butanol is exposed to the deoxygenation catalyst at a temperature between 275° C. and 350° C., and the hydrocarbons comprise a mixture of aromatics, unbranched olefins, and branched olefins; or
 the 2-butanol is exposed to the deoxygenation catalyst at a temperature within a range of 350° C. to 500° C., and the hydrocarbons comprise at least 40% aromatic hydrocarbons.
11. The method of claim 8, wherein the hydrocarbons comprise olefins, the method further comprising exposing the olefins to a subsequent hydrogenation catalyst to form saturated hydrocarbons.
12. The method of claim 1, wherein the acidic catalyst is disposed within a first column, the hydrogenation catalyst is disposed within a second column, and the method further comprises:
 flowing the aqueous composition comprising 2,3-butanediol through the first column to produce the intermediate composition; and
 concurrently flowing the intermediate composition and hydrogen through the second column to produce the composition comprising 2-butanol.
13. The method of claim 12, further comprising concurrently flowing hydrogen through the first column with the composition.

14. The method of claim 12, wherein a deoxygenation catalyst is disposed within a third column, and the method further comprises flowing the composition comprising 2-butanol through the third column to produce hydrocarbons.

15. The method of claim 14, wherein the hydrocarbons comprise olefins, a hydrogenation catalyst is disposed within a fourth column, and the method further comprises flowing the hydrocarbons through the fourth column to produce saturated hydrocarbons.

16. A method, comprising:
converting 2,3-butanediol to hydrocarbons by
flowing an aqueous composition comprising 50-95 wt % 2,3-butanediol through an acidic catalyst bed disposed in a first column to produce an intermediate composition comprising methyl ethyl ketone,
flowing the intermediate composition and hydrogen concurrently through a hydrogenation catalyst bed disposed in a second column to produce a composition comprising 2-butanol, and
flowing the composition comprising 2-butanol through a deoxygenation catalyst bed disposed in a third column to produce hydrocarbons.

17. The method of claim 16, wherein the hydrocarbons comprise olefins, the method further comprising flowing the hydrocarbons through a subsequent hydrogenation catalyst disposed in a fourth column to produce saturated hydrocarbons.

18. A method, comprising:
concurrently flowing hydrogen and an aqueous composition comprising 50-95 wt % 2,3-butanediol through a column including an acidic catalyst bed and a hydrogenation catalyst bed positioned distal to the acidic catalyst bed to produce a composition comprising 2-butanol.

19. The method of claim 18, wherein the column further includes a deoxygenation catalyst bed positioned distal to the hydrogenation catalyst bed, and flowing the composition comprising aqueous 2,3-butanediol through the column produces a composition comprising hydrocarbons.

20. The method of claim 19, wherein the column further includes a subsequent hydrogenation catalyst bed positioned distal to the deoxygenation catalyst bed, and flowing the composition comprising aqueous 2,3-butanediol through the column produces a composition comprising saturated hydrocarbons.

\* \* \* \* \*